US006716972B2

(12) United States Patent
Miller et al.

(10) Patent No.: US 6,716,972 B2
(45) Date of Patent: Apr. 6, 2004

(54) METHOD FOR BREEDING AND GENOTYPING CHICKENS AND PROBES THEREFOR

(75) Inventors: Marcia M. Miller, Altadena, CA (US); Ronald M. Goto, Anaheim, CA (US)

(73) Assignee: City of Hope, Duarte, CA (US)

( * ) Notice: Subject to any disclaimer, the term of this patent is extended or adjusted under 35 U.S.C. 154(b) by 27 days.

(21) Appl. No.: 09/870,521

(22) Filed: Jun. 1, 2001

(65) Prior Publication Data

US 2002/0051989 A1 May 2, 2002

Related U.S. Application Data

(60) Provisional application No. 60/208,471, filed on Jun. 2, 2000.

(51) Int. Cl.$^7$ .................. C07H 21/02; C07H 21/04; C12Q 1/68

(52) U.S. Cl. .................. 536/23.1; 536/24.3; 435/6

(58) Field of Search .................. 435/6; 536/23.1, 536/24.3

(56) References Cited

U.S. PATENT DOCUMENTS

| | | | |
|---|---|---|---|
| 5,451,670 A | 9/1995 | Miller | ............ 536/24.31 |
| 5,536,821 A | 7/1996 | Agrawal et al. | |
| 6,075,125 A | * 6/2000 | Bacon et al. | |

FOREIGN PATENT DOCUMENTS

| | | |
|---|---|---|
| EP | 0 866 135 A2 | 9/1998 |
| FR | 2771422 | 11/1997 |
| WO | 9927132 | 6/1999 |

OTHER PUBLICATIONS

Shiina et al. Immunogenetics 49:384–394 (May 1999).*
Aeed et al. "Influence of different B–complex recombinants on the outcome of Rous sarcomas in chickens" *Animal Genetics* 24:177–181 (1993).
Chaussé et al., "Molecular genotyping of four chicken B–complex haplotypes with B–L$_\beta$, B–F, and B–G probes," *Immunogenetics* 29:127–130 (1989).
Goto, R. et al., "Isolation of a cDNA clone from the B–G subregion of the chicken histocompatibility (B) complex," *Immunogenetics* 27:102–109 (1988).
Heath, E.M., "Developing DNA–Based MHC Typing Reagents for Commercial White Leghorn and Broiler Strains,", *Poult. Sci.* 73 (Supp 1):5 (1994).
Juul–Madsen et al., "New chicken *Rfp–Y* haplotypes on the basis of *MHC* RFLP and MLC analyses," *Immunogenetics* 45:345–352 (1997).
Lamont, S.J. "The chicken major histocompatibility complex and disease," Rev. sci. tec. Off. int. Epiz., 17(1):128–142 (1998).

Li et al., "The MHC of a broiler chicken line: serology, B–G genotypes, and *B–F/B–LB* sequences," *Immunogenetics* 49:215–224 (1999).
Miller, M. et al., "Genotyping chickens for the *B–G* subregion of the major histocompatibility complex using restriction fragment length polymorphisms," *Immunogenetics* 28:374–379 (1988).
Orita et al. "Rapid and sensitive detection of point mutations and DNA polymorphisms using the polymerase chain reaction" *Genomics* 5:874–879 (1989).
Oto et al. "Optimization of nonradioisotopic single strand conformation polymorphism analysis with a conventional minislab gel electrophoresis apparatus" *Analytical Biochemistry* 213:19–22 (1993).
Pharr, G.T. et al., "Identification of *Rfp–Y* (*Mhc*–like) Haplotypes in Chickens of Cornell Lines N and P," J. Hered. 88(6):504–512 (1997).
Vallejo, R.L. et al., "Non–association between *Rfp–Y* major histocompatibility complex–like genes and susceptibility to Marek's disease virus–induced tumours in $6_3 \times 7_2 F_2$ intercross chickens," *Animal Genetics* 28:331–337 (1997).
Wakenell et al. "Association between the *Rfp–Y* haplotype and the incidence of Marek's disease in chickens," *Immunogenetics* 44:242–245 (1996).
Briles, W.E. et al., Genetics, 35:633–652 (1950).
Pink, J.R.L. et al., Immunogenetics, 5:203–216 (1977).
Guillemot, F. et al., EMBOJ, 7:2775–85 (1988).
Lamont, S.J. et al., Poult. Sci., 69:1195–1203 (1990).
Shuman, R.M. et al., "Development of an MHC Typing Test Using DNA Amplification and Oligonucleotide Probes," Poult. Sci., 72 (Suppl. 1):10 (Abstr.) (1993).
Miller, M.M. et al., "PCR–SSCP: a method for studying the polymorphism of the B–G antigens of the chicken major histocompatibility complex," Avian Immunology in Progress 62:153–158, Aug. 31–Sep. 2, 1993.
Briles, W.E. et al., "A polymorphic system related to but genetically independent of the chicken major histocompatibility complex," Immunogenetics, 37:408–414 (1993).

(List continued on next page.)

*Primary Examiner*—Ethan Whisenant
(74) *Attorney, Agent, or Firm*—Rothwell, Figg, Ernst & Manbeck

(57) ABSTRACT

Disease resistance in domesticated fowl, and in particular, chickens, has been associated with certain alleles of the Rfp-Y and B systems of major histocompatibility genes in the birds. This invention provides a method of genotyping chickens which is useful for different breeds of chickens raised for meat and eggs. Methods for selecting disease-resistant chickens and for breeding disease-resistant chickens are also provided. The invention provides oligonucleotide probes for use in the methods. The haplotyping method can be used to select for breeding chickens having a reduced incidence and/or severity of disease, for example, Marek's disease and greater vigor and fecundity.

12 Claims, 9 Drawing Sheets

OTHER PUBLICATIONS

Miller, M.M. et al., Two Mhc and two Mhc genes map to the chicken Rfp–Y system outside the B complex, Proc. Natl. Acad. Sci. USA, 91:4397–4401 (1994).

Zoorob, R. et al., Eur. J. Immunol., 23:1139–45 (1993).

Bacon, L.D. and Witter, R.L., Avian Diseases, 36:378–85 (1992).

Bacon, L.D. and Witter, R.L., J. Hered., 86:269–73 (1995).

Wittzell, H. et al., Immunogenetics, 42:68–71 (1995).

Kroemer, G. et al., Immunogenetics, 31:405–409 (1990).

Blasczyk et al., "Complete subtyping of the HLA–A locus by sequence–specific amplification followed by direct sequencing or single–strand conformation polymorphism analysis," Tissue Antigens, 46:86–95 (1995).

Briles, W.E. et al. Animal Genetics, 25(Supp 2):18 (1994).

Schat, K.A. et al., Avian Pathol., 11:593–605 (1982).

Luna, L.G.; Manual of Histologic Staining Methods of the Armed Forces Institute of Pathology, 3rd Ed., McGraw–Hill Book Co., New York, pp. 32–46 (1968).

Goto, R. et al., Animal Genetics, 25 (Supp. 2):21 (1994).

Kean et al., "Differences in major histocompatibility complex frequencies after multitrait, divergent selection for immunocompetence," Poultry Science 73: 7–17 (1994).

Davidson et al., "PCR diagnosis of Marek's disease, reticuloendotheliosis and lyumphoid leukosis in chickens and turkeys," PCR: A Diagn. Hum. Anim. Virus Dis., 543–552 (1995).

Afanassieff, M. et al., Abstract presented at the Avian Immunology Research Group Meeting, Obergurgal, Austria, Apr. 21–24, 1996.

Jarvi, S.I. et al., Immunogenetics, 43:125–135 (1996).

Miller, M.M. et al., Proc. Natl. Acad. Sci. USA, 93:3958–3962 (1996).

Kaufman et al., "The 'Minimal Essential MHC' revisited: both peptide–binding and cell surface expression level of MHC molecules are polymorphisms selected by pathogens in chickens," Hereditas 127:67–73 (1997).

Afanassieff, Marielle, et al., "At least One Class I Gene in Restriction Fragment Pattern–Y (Rfp–Y), the Second MHC Gene Cluster in the Chicken, Is Transcribed, Polymorphic, and Shows Divergent Specialization In Antigen Binding Region," *The journal of Immunology* 166:3324–3333, 2001.

Database EMBL 'Onlinel, Chicken MHC Rfp–Y Gene YFV–Y–FVW7, Database Accession No. AF218784, XP002230335, Mar. 9, 2001 (Abstract).

Database EMBL 'Online?, Chicken mRNA Sequence, Database Accession No. Al980256, XP002230334, Sep. 17, 1999 (Abstract) of Tirunagaru, Vijaya Gourl, et al., "An Expressed Sequence Tag Database of T–Cell–Enriched Activated Chicken Splenocytes: Sequence Analysis of 5251 Clones," *Genomics* 66:144–151, 2000.

\* cited by examiner

*α1 domain*

```
              10.       20.       30.       40.       50.       60.       70.       80.
YFVw*7   GSHSLRYFLTGMTDPGPGMPRFVIVGYVDDKIFGTYNSKSRTAQPIVEMLPQEDQEHWDTQTQKAQGGERDFDWNLNRLPERYNKSK
BFIV*12  EL-T---IQ-A-------Q-W--T-----GEL-VH-N-TA-RYV-RT-WIAAKA--QY--G---IG--N-QIDRE--GI-QR---QTG
```

*α2 domain*

```
         90.       100.      110.      120.      130.      140.      150.      160.      170.
YFVw*7   GSHTMQMMFGCDILEDGSIRGYDQYAFDGRDFLAFDMDTMTFTAADPVAEITKRRWETEGTYAERWKHELGTVCVQNLRRYLEHGKAALKRR
BFIV*12  ----V-W-Y------G-P----Y-M-Y-----T---KG-------V-E-VP---K--E-SE/P----NY-EET--EW----V-Y---E-G--
```

*α3 domain*

```
      180.      190.      200.      210.      220.      230.      240.      250.      260.      270.
YFVw*7   VQPEVRVWGKEADGILTLSCHAHGFYPRPITISWMKDGMVRDQETRWGGIVPNSDGTYHASAAIDVLPEDGDKYWCRVEHASLPQPGLFSW
BFIV*12  ER-----------------R---------VV--L---A--G-DAHS------G-----TWVT--AQ-G-----Q------------Y--
```

*Transmembrane domain*

```
              280.      290.      300.
YFVw*7   EP/QPNLIPIVAGAVVAIVAV/IAAVVGLVVWKSKS
BFIV*12  --P----V-----VA-----IA-MVG--FIIYRRHA
```

*Cytoplasmic domains*

```
         310.      320.      330.
         GKEKKGYEAAAGHDGESSGSATGSEPSI
         --KG---NI-PDRE-G--S-S---N-A-
```

Figure 4

```
GGTGTTGGATTCATCATCTACAGACGCCACGCAGGTAAAAGCAGAGGGGTGCAGGCGGGCAGTGGTGGCAGTGGGGGGATCTG
GGTCCCCCTTGGGAGCCCTCAGCCTGGCTGTGATGTGAACCTGTGTTGATTCATCTCTCTGTCTGCAGGGAAGAAGGGGAAGG
GCTACAACATCGCGCCCGGTGAGTGATGAGGGCAGCGCTGTCCCCCACCTCTGCCCAGTGCCAGGGCGGTCCTgGGGTCTGCA
CTTTCTCCCAGGGTACCCATTCCTGGTGCTTGGGGCTGCTCCACGCCCCATAGGGAGCACAGGGCTGGGTCTCACAGCTGTTC
CTCCCTTATAGACAGGGAAGGTGGATCCAGCAGCTCGAGCACAGGTGCGGTGTGGGGCTGTGGGTTGGGAGGGGTCCGTGTGC
TCTCTGTGGTACTGCCCAGGGCTGGGCTATGCTGGGGCTCTGCGGGGAGACCCCCGGAGCAGAGGGTTGGGATGTGAACATGG
GCCCCGTGGGACACCATCTCTTCTCATCCCCACAGGGAGCAACCCCTCCATCTGAGTGCTGTGCTTCAGCATGCACGAAGCCA
ACAGTCCACACCAGCATTTGGGGTCAGTGATGGGCACAGCCCCATCCTCTTGACCTCTCACATCTCGTTCTGCTTCCTATGCT
GACTGTTATGC
```

Figure 5

```
GGGGAGAAAGCGGGAGCTGCAGGTGGGGCCTGGACCCCCTTGGGAATGCCCATGTTCTGACATGAGCTTAATGTTCACACTTC
TTTCTATCTGTAGGGAAGGAGAAGAAGGGTTATGAAGCAGCGCCAGGTGAGTGCCAAGGGCAGCGCTTTACCCTGCCAGTGCT
TGGGGTCAGGGCACTCTGGGGCCCCTCGTTGCTTTTGGGGTCACAGTGCAGGTGGTGGCATGATGCTCCATGCCCCACAGCGA
GCACAGAGCCAGGGCTCATGGCTCTCCCTCCCTTGCAGGCCAGGGCGGAGAATCCAGCATATCGGCCACAGGTATAgTGTGGA
ATGGGGGTTCAGGAGGGGTCCCTGTGGTTGGAGCATTCCCAGtTCCCTGCACTCCCCTGTTGGACCCACGGCCGGGGCAATAC
TGGGCCcAaCCCTCCCTGGAGAAcCCCCAGGGTGGTGAGTCGGGACGGGGACGTGGTCCCATATGACACCACCTCTTCTCACC
CGCACAGGAAGTGAACTTCCCTTCTGAGTGCTGTGTTACTTCAGCCAGCCCTGCATGCATGTGTTTGGAGTGTGTGGGTGTGT
GTATCTCAGTGTGTGCTCAACTTCCTGCATCTCCTCGGGCTGACA
```

METHOD FOR BREEDING AND GENOTYPING CHICKENS AND PROBES THEREFOR

RELATED APPLICATIONS

This application claims priority from copending provisional application Serial No. U.S. 60/208,471, filed Jun. 2, 2000.

GOVERNMENT RIGHTS STATEMENT

This invention was funded in part by the United States Department of Agriculture under the USDA National Research Initiative Competitive Grants Program (92-37204-8244), USDA Federal Assistance Program Agreement No. 58-3148-5-023 and the National Science Foundation (MCB-9604589). The United States government may have certain rights in the invention.

BACKGROUND OF THE INVENTION

1. Technical Field

This invention relates to determining the genotype of chickens.

2. Description of the Background Art

The poultry breeding business is of major economic importance in the United States and in most parts of the world. Epidemics of viral infectious disease, for example Marek's disease, in flocks raised for meat or eggs can have a devastating effect to this industry, even in modern facilities. Consequently, development of methods to produce breeding stocks of chickens, whether raised for meat or eggs, which are resistant to disease, is commercially very important.

In chickens, as opposed to most mammals, the particular Mhc haplotypes have readily demonstrated differential influences in the immune response to certain diseases, such as the tumors caused by the highly infectious herpes virus responsible for Marek's disease. Chickens with different Mhc genotypes respond differently to the infectious pathogen of Marek's disease, with potentially deadly consequences to animals possessing a relatively unresponsive Mhc genotype (i.e., two non-protective haplotypes). Determining the Mhc genotype of chickens has therefore become important to the poultry industry, so that disease-resistant strains of chickens can be bred.

In domesticated fowl, the known Mhc genes are organized into two separate linkage groups, B and Rfp-Y. FIG. 1 provides a schematic map showing the known chicken Mhc genes. The B system comprises polymorphic classical Mhc class I heavy chain, class II beta chain, B-G genes and other genes. The B system has been known as a highly polymorphic blood group system since the early 1940's. Rfp-Y was discovered more recently by DNA hybridizations (Briles et al., *Immunogenetics* 37:408–414 (1993)) and consists of at least two class I heavy chain genes, three class II beta chain genes, a c-type lectin gene and two additional genes of unknown nature. Miller et al., *Proc. Natl. Acad. Sci. USA*, 91:4397–4401 (1994); Miller et al., *Proc. Natl. Acad. Sci. USA* 93:3958–3962 (1996).

As with the B region, the Rfp-Y gene region is small. At least one Rfp-Y haplotype contains only a single functionally active class I locus. This suggests that disease associations with particular Rfp-Y haplotypes have a similar basis in a small number of loci. In addition, interactions may occur between alleles of the B and Rfp-Y loci. Particular combinations of haplotypes in the two systems therefore may provide optimal disease resistance for a particular disease.

It has already been observed that when the B system provides intermediate disease resistance to Marek's disease, the influence of Rfp-Y genotype can be significant. Wakenell et al., *Immunogenetics* 44:242–245 (1996). This influence may be a direct one wherein the Rfp-Y genes compensate in antigen presentation, however additional interactions could occur between loci in B and Rfp-Y. For example, studies of Mhc Class I loci in mice have shown that antigen presenting molecules have a critical role in controlling the activity of natural killer (NK) cells. Signal peptides cleaved from nascent classical class I polypeptides are presented by at least one non-classical class I molecule and recognized by receptors on NK cells, resulting in modulation of NK cell activity. Natural killer cells are critical in eliminating infected cells in which class I molecule expression has been down-regulated by the infecting pathogen. Having the capacity to detect B and Rfp-Y haplotypes in commercially bred poultry provides a means by which immune responses can be optimized.

In the chicken, the role of particular Mhc haplotypes in disease resistance has been extensively investigated. The influence of the genotype of the Mhc B system and resistance to certain diseases in chickens, for example, Marek's disease, has been documented by several authors. See Hanson et al., *Poult. Sci.* 46:1268 (1967); Briles et al., *Science* 195:193–195 (1977); Briles et al., *Science* 219:977–979 (1983); Longenecker et al., *Immunogenetics* 3:401–407 (1976); Dietert et al., *Crit. Rev. Poult. Biol.* 3:111–129 (1991); Kaufman et al., *Immunol. Rev.* 167:101–117 (1999). Genotyping of the B complex of chickens, however, has focused mostly on particular lines of White Leghorn birds, a breed raised primarily for egg production. Alloantisera used to determine B haplotypes in particular lines of egg-producing chickens do not work well for B haplotyping in other lines of chickens. This is especially true for those lines used in the production of chickens raised for meat which are genetically somewhat distant from layer lines.

Though the immune response in chickens to Marek's disease and other viral pathogens is strongly influenced by B complex genotype, other alleles at other loci, including the Rfp-Y gene cluster, perhaps the NK region and other more poorly characterized regions as well, influence Marek's disease resistance. See Brown et al., Avian Dis. 28:884–899 (1984); Vallejo et al., *Anim. Genet.* 28:331–337 (1997); Bumstead, *Avian Pathol.* 27:s78-s81 (1998); Kaufman et al., *Avian Pathol.* 28:s82-s87 (1998); Bumstead, *Rev. Sci. Tech.* 17:249–255 (1998); Yonash et al., *Anim. Genet.* 30:126–135 (1999). Rfp-Y haplotypes differentially influence disease resistance and immunity in chickens. For example, Pharr et al. showed, in chickens of Cornell line N, that with birds homozygous for B system haplotype, skin graft rejection was greater and occurred more quickly when donor and recipient were mismatched for Rfp-Y than when they were Rfp-Y compatible. Pharr et al., *Immunogenetics* 45:52–158 (1996). Additionally, there is varied evidence for the ability for Rfp-Y differences to stimulate lymphocyte proliferation in vitro (Pharr et al., *Immunogenetics* 45:52–58 (1996); Juul-Madsen et al., *Immunogenetics* 45:345 (1997)), indicating that alloresponses to Rfp-Y may be induced.

The products of Rfp-Y genes have a structure similar but not identical to classical class I molecules. The sequence variability inherent in the Rfp-Y class I molecules themselves is sufficient to inherently elicit this type of allogeneic response, but alternatively these molecules could present some form of polymorphic antigens that serve as a minor histocompatibility antigen and produce the described histocompatibility effect. The Rfp-Y loci may be important in providing molecules that supplement the apparently less than comprehensive antigen presentation provided by the B system loci. Mhc-like genes located outside classical Mhc gene regions are implicated in a number of immune response functions in mammalian species, including selection of T-cell population during development. Adachi et al., *Proc. Natl. Acad. Sci. (USA)* 92:1200–1204 (1995).

The previous work of Wakenell et al. indicates that Rfp-Y haplotypes influence resistance to the commercially important Marek's disease in the chicken. Studies of Rfp-Y influence on Marek's disease virus challenge have produced results indicating that Rfp-Y haplotype affects susceptibility to infection in different B complex backgrounds. Wakenell et al., *Immunogenetics* 44:242–245 (1996). In this study, data comparing incidence of Marek's disease tumors in chickens carrying three different Y system genes showed that the Rfp-Y system exerts an effect on Marek's disease resistance and that the influence of Rfp-Y haplotypes in some combinations may be quantitatively similar to that of the B-F region. See Wakenell et al., page 244. Some conflicting data that has been reported might be due to the particular B and Y complex interactions either accentuating or masking the Rfp-Y effects. See Vallejo et al., *Anim. Genet.* 28:331–337 (1997).

Genes within B and Rfp-Y both have a demonstrated influence in resistance and susceptibility to a number of diseases, including virally-induced tumors, bacterial infections and infections with protozoan parasites. See, for example, Briles et al., *Science* 195:193–195 (1977); Briles et al., *Immunogenetics* 20:217–226 (1984); Longenecker et al., *Immunogenetics* 3:401–407 (1976); Kaufman et al., *Hereditas* 127:67–73 (1997); Wakenell et al., *Immunogenetics* 44:242–245 (1996); Vallejo et al., *Anim. Genet.* 28:331–337 (1997); Lamont, *Rev. Sci. Tech.* 17:128–142 (1998); Caron et al., *Poult. Sci.* 76:677–682 (1997); Thacker et al., *J. Virol.* 69:6439–6444 (1995); Uni et al., *Br. Poult. Sci.* 36:555–561 (1995); Bacon et al., J. Hered. 86:269–273 (1995); Hlozanek et al., *Virology* 203:29–35 (1994); Schat et al., *Poult. Sci.* 73:502–508 (1994); Nakai et al. *Avian Dis.* 37:1113–1116 (1993); Lamont et al., *Immunogenetics* 25:284–289 (1987); Cotter et al., *Poult. Sci.* 77:1846–1851 (1998).

There are additional studies reported in the literature describing the influence of Mhc haplotype in many poultry diseases, for example the regression of Rous sarcoma virus induced tumors, Marek's disease, infectious laryngotracheitis and coccidiosis. See Yoo et al., *Br. Poult. Sci.* 33:613–620 (1992); Poulsen et al., *Poult. Sci.* 73 (Suppl. 1):108 Abstr. (1994); Poulson et al., *Poult. Sci.* 77:17–21 (1998); Clare et al., *Immunogenetics* 22:593–599 (1985). Since the association of Mhc haplotype with disease resistance in chickens has been demonstrated, the haplotyping methods described below may be used to select for chickens genetically resistant to a variety of diseases.

One of the most important diseases of poultry, in commercial terms, Marek's disease, is caused by a highly contagious herpes virus that induces T-cell lymphomas in chickens. The virus exists in poultry-breeding countries throughout the world and is responsible for tremendous losses to the industry. Because of the strong Mhc B influence on survival of infection with Marek's disease virus, many modern commercial chicken breeders select for or are at least aware of the Mhc B types in their commercial lines. Breeders generally have not been able to test for Rfp-Y genotypes, however.

Vaccination is very effective in reducing losses from Marek's disease, but vaccine breaks do occur and there is evidence that new, more virulent forms of Marek's disease virus appear periodically in vaccinated flocks. Importantly, Mhc haplotypes also influence the efficacy of vaccination in commercial flocks, see Bacon et al., *Poult. Sci.* 73:481–487 (1994); Bacon et al., *J. Hered.* 86:269–273 (1995); Bacon et al., *Avian Dis.* 38:65–71 (1994). Genetic resistance is an important adjunct to vaccination in the prevention of Marek's disease in chickens. Therefore the strategies of selection for beneficial Mhc haplotypes and vaccination may be used together to optimize flock performance. Mhc haplotyping according to this invention may also be used to test for newly-recognized resistant haplotypes so they may be introduced into flocks.

Another disease of consequence in commercially raised chickens is coccidiosis. Coccidiosis is a protozoal disease of poultry and other birds that results in diarrhea, enteritis and weight loss. Coccidiosis occurs everywhere that poultry are raised in large numbers. There are seven valid species of chicken coccidia (*Eimeria acervulina, E. brunetti, E. maxima, E. mitis, E. necatrix, E. praecox* and *E. tenella*) that vary in their pathogenicity. Infections with the causative organisms occur most often in young, rapidly growing birds. Administration of anticoccidial drugs in recent years have reduced some losses, however drug resistant forms of coccidia appear to be developing since losses now are increasing despite the extensive use of drugs.

This phenomenon has led to interest in developing alternative means of infection control of this disease based in immunity. Mhc haplotype has been shown to influence resistance, susceptibility and immunity to Eimeria. See for example, Caron et al., *Poult. Sci.* 76:677–682 (1997), Brake et al., *Infect. Immun.* 65:1204–1210 (1997); Nakai et al., *Avian Dis.* 37:1113–1116 (1993). Mhc haplotype differences are correlated with differences in caecal lesion scores and weight gain during infection. Also, just as with Marek's disease, Mhc haplotype influences the effectiveness of immunizations. Methods of chicken haplotyping therefore can be used advantageously to select birds resistant to coccidiosis or with improved immune response to Eimeria ssp. upon vaccination.

Another acute viral disease of commercial importance is laryngotracheitis. This disease currently is managed by strict separation of susceptible flocks and by vaccination. Particular Mhc B haplotypes have been found to differ significantly in their influence in laryngotracheitis. As with Marek's disease, laryngotracheitis is caused by a herpes virus and immune responsiveness apparently is a component of susceptibility to this disease as well. Again, as with Marek's disease, Mhc haplotype influences the efficacy of vaccination against laryngotracheitis (birds of some haplotypes require higher dosage of vaccine to achieve protection). Poulsen et al., *Poult. Sci.* 73 (Suppl. 1):108 Abstr. (1994); Poulson et al., *Poult. Sci.* 77:17–21 (1998).

Genes located within chicken Mhc regions have significant effects on the immune response to pathogens that can be detected experimentally. For example, the capacity of chickens to regress tumors caused by avian leukosis virus is associated with the capacity of T cells to respond to the presentation of Mhc restricted antigen. Thacker et al. *J. Virol.* 69:6439–6444 (1995). A number of the standard and recombinant B haplotypes have been categorized as either progressor or regressor haplotypes. Brown et al. *Immunogenetics* 19:141–147 (1984); Collins et al. *Poult. Sci.* 64:2017–2019 (1985); Taylor et al. *Anim. Genet.* 19:277–284 (1988); Lukacs et al. Poult. Sci. 68:233–237 (1989); Aeed et al. *Anim. Genet.* 24:177–181 (1993); White et al. Poult. Sci. 73:836–842 (1994). In the Rous sarcoma virus experimental system, immunity is v-src-specific. Gelman et al., *Cancer Res.* 53:915–920 (1993); Plachy et al., *Immunogenetics* 40:257–265 (1994). There is evidence that B haplotype is also associated with shedding of avian leukosis group-specific antigen and hence may influence susceptibility to post-hatching infection from other infected birds. Yoo et al., *Br. Poult. Sci* 33:613–620 (1992).

Further associations between Mhc haplotype and resistance to two bacterial pathogens—fowl cholera and salmonella are reported. Lamont et al., *Immunogenetics* 25:284–289 (1987); Cotter et al., *Poult. Sci.* 77:1846–1851 (1998). These reports demonstrate the importance of Mhc haplotype to immunity in chickens against several commercially important diseases and to the important experimental model, Rous sarcoma virus, and suggest that genetic selection for particular Mhc haplotypes is valuable to breeders for the production of both individuals and flocks that are resistant to numerous diseases.

Selection for B haplotypes providing resistance to Marek's disease is performed by a number of companies breeding chickens for the production of eggs. Generally, selection is done on the basis of the results of hemagglutination assays using alloantisera that have been developed for particular breeding lines within the company's flocks. These serological typing methods can be applied to birds within a population once appropriate serological reagents have been developed, however alloantisera made in one population are usually not useful to type other populations. See Li et al., *Immunogenetics* 49:215–224 (1999). Because most of the alloantisera currently available were prepared for chickens bred for eggs (primarily the White Leghorn breed), there are few reagents available for haplotyping other breeds of chickens.

Development of appropriate alloantisera is a lengthy procedure, generally requiring several years. In addition, the genetic background of the birds, including at least some information with respect to other blood group systems, should be known before the alloantisera are produced. This requirement poses a major disadvantage. In the past, the genetics of birds used as donors and recipients in the immunizations to produce alloantisera have been surmised by initial approximations of the genetic differences using alloantisera from other flocks. The alloantisera specific for a particular flock must be made by reciprocal immunizations between sire and dam in fully pedigreed stock, and then tested by hemagglutination assay among the fully pedigreed progeny of the birds that served as donors and recipients in the immunizations. Cross-reactivity among B haplotypes is commonly encountered, necessitating appropriate adsorptions of the sera to enhance their specificity for the individual Mhc B haplotypes. Because any alloantiserum potentially contains antibodies to a number of polymorphic cell surface markers, considerable care must be taken in typing poorly characterized flocks. Accurate results require considerable attention to detail.

The existing serological reagents from egg-producing chickens are not useful in other chicken breeds. Mhc marker assisted selection for Marek's disease resistant broiler chickens is not performed routinely, in part because of the lengthy effort needed to develop typing methods based on alloantisera and in part because of the breeding methods used to maintain broiler breeder stock. Therefore, a simple method for Mhc haplotyping for these birds is not currently generally available. No serological reagents exist for the Rfp-Y system in any breed of chicken. The B system and the Rfp-Y system of chickens of all breeds, even those not belonging to the White Leghorn breed, can be studied advantageously using the inventive methods and probes, allowing Mhc marker assisted selection to be applied in selecting for additional disease resistance in breeding stock.

DNA-based typing methods, although currently more expensive on a per test basis, have obvious advantages in that nucleotide probes can be used to determine Mhc haplotypes in flocks without the enormous investment of time and labor required to make alloantisera. One such method relies on the patterns of B-G gene restriction fragments revealed in genomic DNA digested with a restriction enzyme and analyzed by Southern hybridization with nucleic acid probes for the B-G genes. See Miller, U.S. Pat. No. 5,451,670. An advantage of this type of approach is that prior knowledge of gene sequences is not necessary. Another method relies on gene restriction fragment patterns revealed in genomic DNA digested with several restriction enzymes and analyzed by Southern hybridization with non-system-specific nucleic acid probes for the B-F and B-L genes. See Lamont, S. J. et al., *Poult. Sci.,* 69:1195 (1990). Yet another similar method is based on hybridization of oligonucleotide probes specific for known sequences in the various alleles of the B system class I gene. See Heath et al., Poult. Sci. 73(Suppl 1):5 (1994).

Various applications of Southern hybridization with B system probes have been reported in the literature. See Chausse et al., *Immunogenetics* 29:127–130 (1989); Goto et al., *Immunogenetics* 27:102–109 (1988); Miller et al., *Immunogenetics* 28:Z374–379 (1988); Briles et al., *Immunogenetics* 37:408–414 (1993); Pharr et al., *J. Hered.* 6:504–512 (1997). The B-G gene probes which are useful in ascertaining B haplotypes because of their close linkage to B class I and class II loci are often sufficient in known stocks of birds for the assignment of B haplotype. The B-F and B-L probes are useful in revealing polymorphic restriction fragment patterns, but they show cross hybridization (recognition) with genes both in B and Rfp-Y gene clusters since each of the B-F and B-L probes were developed without knowledge of sequence differences in the B and Rfp-Y genes.

Because the class I and class II genes in Mhc B and Rfp-Y are fairly closely related, probes for the B system crosshybridize to varying degrees with Rfp-Y genes. It therefore is difficult to use these methods to type birds for polymorphisms in either system in the presence of polymorphisms that are contributed by the other system. For this reason, the probes initially used to identify the Rfp-Y cluster were B system probes able to hybridize to genes in both the Rfp-Y and B gene clusters. Because of the crossreactivity, these types of tests often cannot provide useful Rfp-Y data unless analysis is performed on fully pedigreed families of birds and B-G typing is also performed. Otherwise it is not possible to distinguish which restriction fragments result from each system. Indeed, the presence of Rfp-Y was only found because fully pedigreed animals happened to be the subject of a study with another objective.

DNA-based Mhc typing based on specific sequences may be used, however one must have some sequence data for genes within each haplotype in the population to be tested. This requirement is a major stumbling block to development of an easy, comprehensive haplotyping method for B and Rfp-Y system genes. It is difficult, at least initially, to obtain complete haplotype information about a particular bird using these methods without making sequence determinations for each allele at each locus chosen to represent the entire haplotype.

The use of a technique known as polymerase chain reaction, single-stranded conformational polymorphism ("PCR-SSCP") has been proposed to study the expression of genes in non-erythroid tissues. Miller, M. M. and Goto, R. M., *Avian Immunology in Progress*, Tours (France), Aug. 31–Sep. 2, 1993, Ed. INRA, Paris 1993 (Les Colloques, No. 62); Zoorob et al., PCT/FR98/02501. In this method, short segments of genes of interest are amplified using the PCR. The PCR products are then heat denatured and applied to a non-denaturing polyacrylamide gel. The single-stranded fragments of the heat-denatured DNA fragments assume secondary conformations determined by their sequences and migrate differently in the polyacrylamide gel during electrophoresis, producing a pattern (or fingerprint) representative of the sequences within the genome in the region of amplification. For this method, oligonucleotide primer sets that hybridize to conserved sequence sites surrounding the polymorphic regions must be developed for the different alleles to be typed. Therefore, a certain amount of knowledge regarding the structure of the genes to be studied is required. PCT application PCT/FR98/02501 discloses methods of detecting Mhc genes in birds such as chickens which are related to resistance to virally-induced tumors, for selection of animals having a desired genotype. Specific nucleic acid probes are disclosed which are able to discriminate between genes of the B and Rfp-Y systems.

Currently, there are no commercially available tests to determine the haplotype in the Rfp-Y system. There are no alloantisera. Consequently, a test which would allow breeders, researchers, and others to rapidly determine the haplotype of birds using relatively straightforward techniques is needed. An ideal test would be quick, simple to perform, and avoid the need for specialized equipment beyond that commonly found in a molecular biology laboratory. The test would not require alloantisera which might not be available for use in all birds or detailed knowledge of the genetics of the birds to be tested. Such a test which could determine the haplotype in the Rfp-Y system as well as the B system using a single set of reagents for each system would be highly desirable, and could be used to aid in breeding birds with increased resistance to disease.

SUMMARY OF THE INVENTION

Accordingly, the present invention provides the probes of SEQ ID NO: 1 and 2, and probes which contain at least about 17 consecutive nucleotides of these sequences and are about 17 to about 1,000 nucleotides in length. Preferred probes are about 100 to about 1,000 nucleotides in length. Most preferred probes are those of SEQ ID NOS: 1 and 2. Probes which are fragments of SEQ ID NOS: 1 and 2 are contemplated by the invention, from about 17 nucleotides to one nucleotide less than the entire sequence. Probes which are at least about 70% homologous, or preferably at least about 90% homologous to SEQ ID NOS: 1 and 2 are also provided. Because of the nature of DNA hybridization, higher degrees of homology are required for shorter probes; e.g., only a perfect match or a single nucleotide mismatch is preferred for probes of minimum (about 17 nucleotides) length.

The invention provides methods for breeding chickens to produce disease-resistant offspring by selecting a disease-resistant chicken for mating using these probes. The method involves providing a genomic DNA sample from at least one chicken, digesting the sample with one or more restriction endonucleases to obtain restriction fragments and resolving the restriction fragments, preferably by electrophoresis. The resolved fragments are then optimally transferred to one or more hybridization membranes and optionally immobilized there. The resolved fragments are then incubated with a labeled probe as described above such that the probe hybridizes. Unhybridized probe is removed and an image of the labeled hybridized probe is created, to form a restriction fragment pattern. From this restriction fragment pattern, the Mhc genotype of the chicken providing the DNA sample is determined. If desired, the probe can be stripped and a second probe used in the same manner to create a second restriction fragment pattern.

In a preferred embodiment, the resolved restriction fragments from the genomic DNA sample of a single bird are probed twice, once with a probe specific for the Rfp—Y system and one specific for the B system of the chicken Mhc. Most preferably, the probes of SEQ ID NOS: 1 and 2 are used sequentially or on parallel samples of genomic DNA from the same chicken. Once the Mhc genotype of a chicken has been determined, the genotype is correlated with disease-resistance and a chicken having an Mhc genotype which correlates with disease-resistance is selected for mating. The selected chicken is mated with a second chicken of opposite gender. Preferably, the second chicken has also been selected for a Mhc genotype correlating with disease resistance according to the invention. The invention also provides methods for selecting chickens which are disease-resistant as described above, and methods for determining the Mhc genotype of chickens as described above.

BRIEF DESCRIPTION OF THE DRAWINGS

FIG. 2 provides an alignment of the Y-FVw*7 (SEQ ID NO: 5) and B-FIV*12 (SEQ ID NO: 6) gene sequences. The "-" indicates sequence identity. The "/" indicates a gap inserted to optimize sequence alignments.

FIG. 3 depicts the alignment of the deduced amino acid sequences of Y-FVW*7 (SEQ ID NO: 3) and B-FIV*12 (SEQ ID NO: 4) to illustrate regions of greatest sequence difference between the B and Rfp-Y class I loci. The "-" indicates sequence identity. The "/" indicates a gap inserted to optimize sequence alignments.

FIG. 4 provides the sequence of the 178/179f probe for B class I genes (SEQ ID NO: 2).

FIG. 5 provides the sequence of the 163/164f probe for Rfp-Y class I genes (SEQ ID NO: 1).

DETAILED DESCRIPTION OF THE INVENTION

Figure 1:
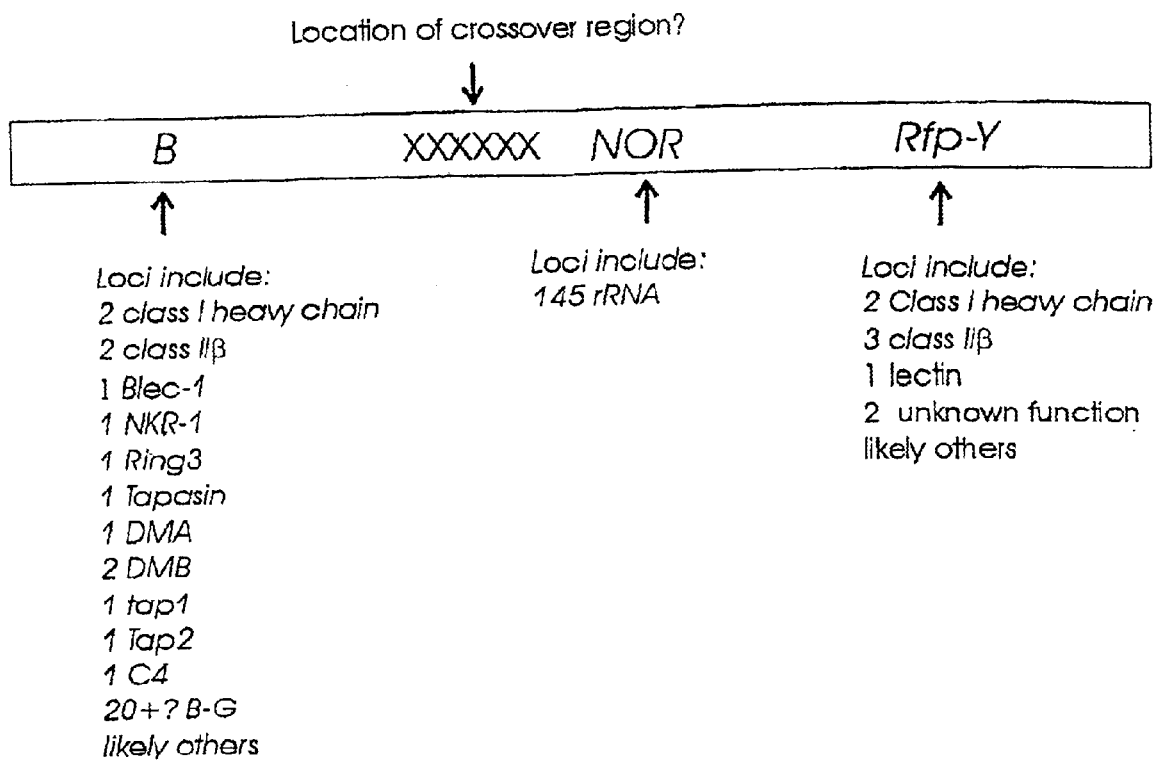
FIG. 1 provides a schematic map of chicken Mhc genes.

The two B class I loci, represented by B-FI*12 and B-FIV*12, are highly similar to each other (94% identity in nucleotide sequence). The two Rfp-Y class I genes, represented by Y-FVw*7 and YFVIw*7, also are nearly identical (94%) with the exception of a large hexanucleotide repeat sequence (48 copies of the hexanucleotide GGGCTG (SEQ ID NO: 11) in the exon 1 sequence of Y-FVIw*7. Because the two loci in each system are very similar to each other, aside from this repeat, the Y-FVw*7 and B-FIV*12 were chosen as representative for the loci in each system and used in sequence analysis.

Figure 2A:
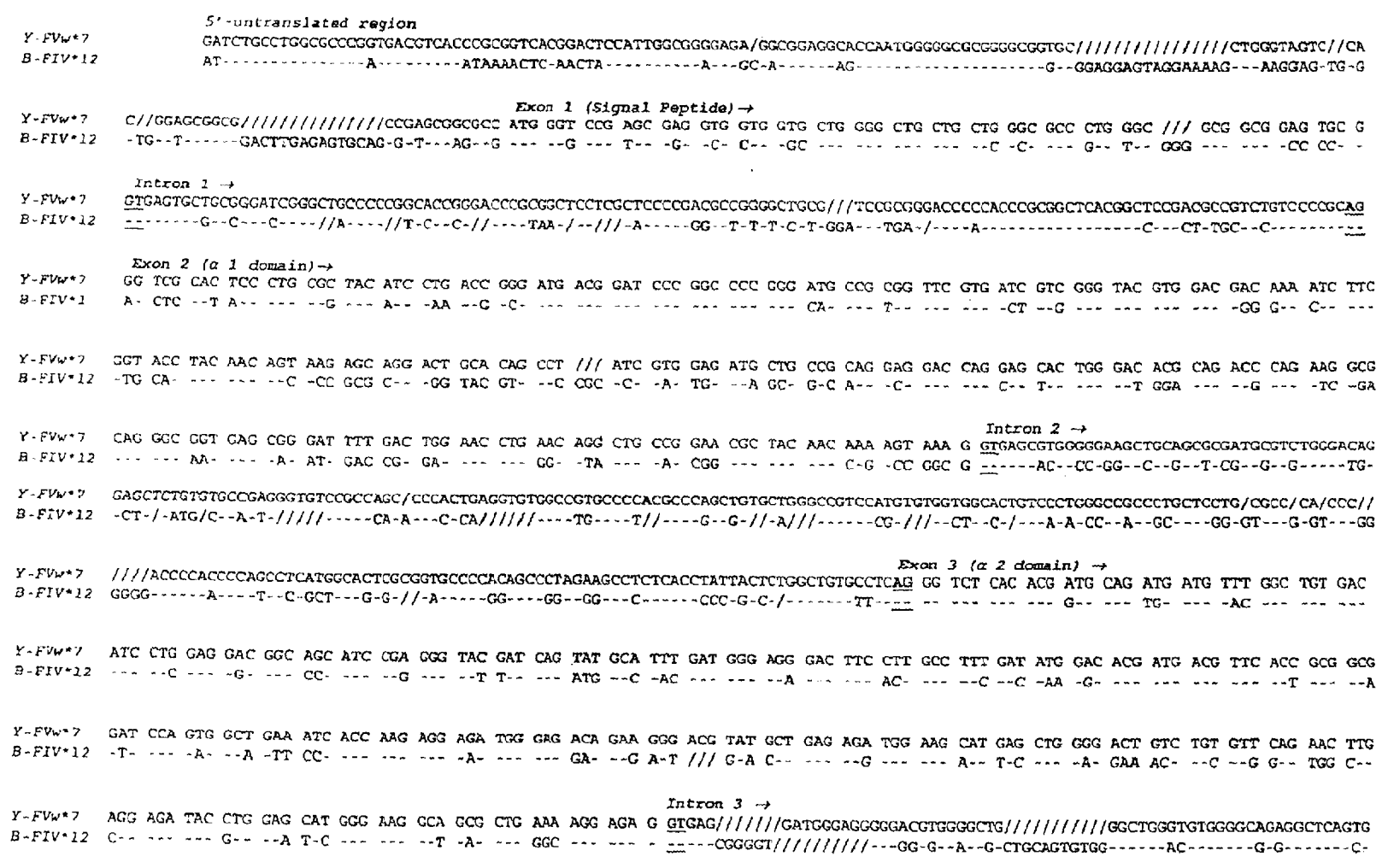
Figure 2B:
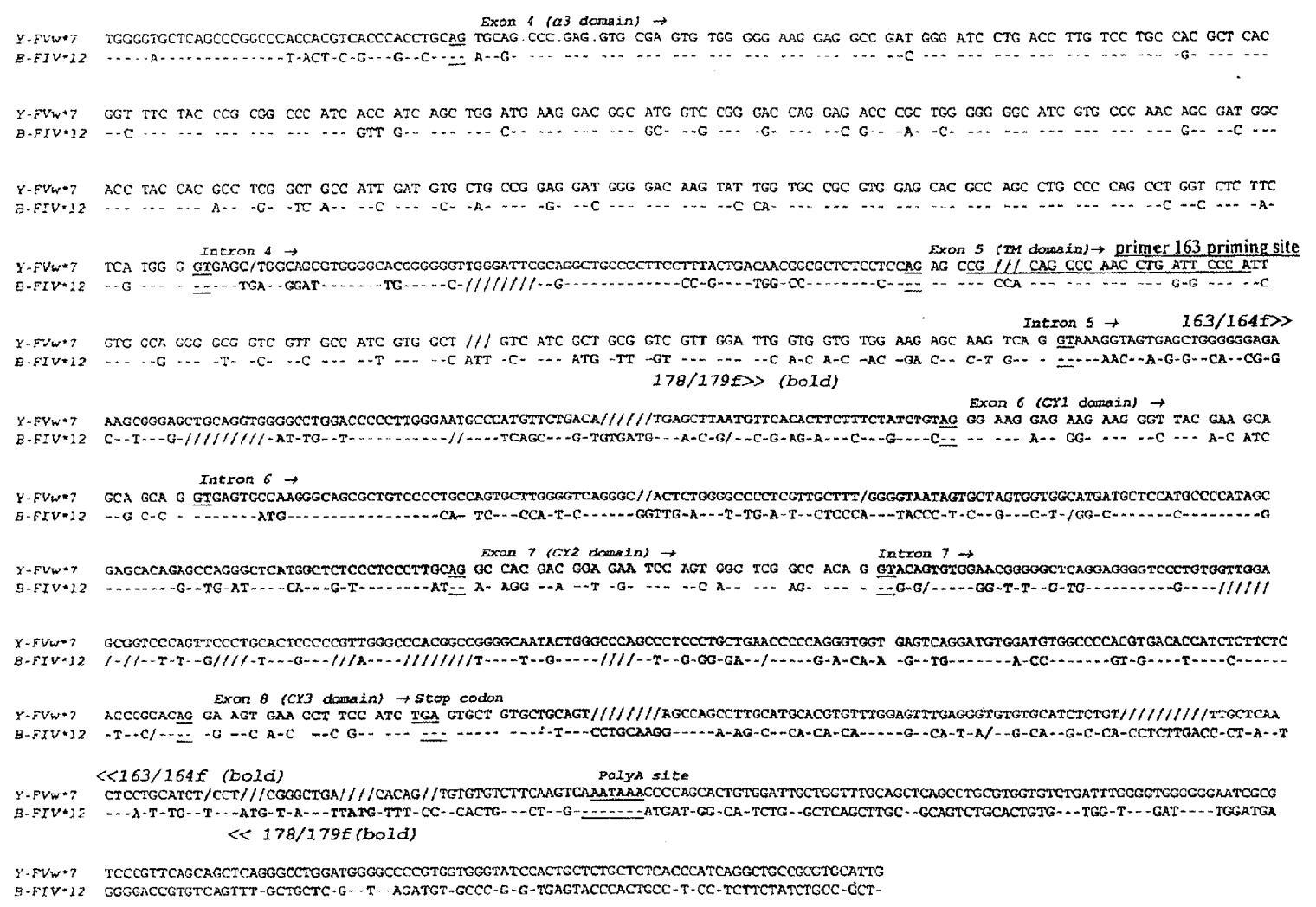

Because of the time-consuming process required to determine the Rfp-Y genotype of a bird using the cross-hybridizing B probes, and the increasing use of haplotyping by Southern hybridization both for experimental and commercial purposes, the sequences of the Rfp-Y and B class I loci (represented here by Y-FVw*7 and B-FIV*12; see FIG. 2) were aligned and examined for regions where the loci were most divergent, with the goal of developing system-specific probes. The alignments compared in Table 1 demonstrate that the genes generally share greater similarity at their 5'-ends and mid-sections, especially in exon sequences, and diverge more at the 3'-end.

TABLE 1

Sequence Similarity Comparisons Between Different Segments of the Y-FVw*7 and B-FIV*12 Genes

| Gene region/domain Y-FVw*7 vs. B-FIV*12 | Length (bp) Y-FVw*7 | Length (bp) B-FIV*12 | DNA Similarity Index[1] (S.I.) | Amino acid Similarity Index[2] (S.I.) |
|---|---|---|---|---|
| 5'UT | 124 | 162 | 56 | — |
| Ex1/sp | 63 | 66 | 72 | 56 |
| IN1 | 126 | 117 | 66 | — |
| Ex2/α1 | 261 | 264 | 66 | 49 |
| IN2 | 245 | 226 | 44 (58)[3] | — |
| Ex3/α2 | 276 | 273 | 59 | 64 |
| IN3 | 95 | 103 | 68 | — |
| Ex4/α3 | 273 | 273 | 86 | 77 |
| IN4 | 80 | 71 | 65 | — |
| Ex5/TM | 102 | 108 | 59 | 51 |
| IN5 | 114 | 110 | 57 | — |
| Ex6/cy1 | 33 | 33 | 49 | 54 |
| IN6 | 157 | 159 | 38 | — |
| Ex7/cy2 | 33 | 33 | NS | 46 |
| IN7 | 185 | 154 | 58 | — |
| Ex8/cy3 | 18 | 18 | NS (67)[4] | 67 |
| 3'UT (to poly A signal) | 127 | 155 | 51 | — |
| 163/164f vs. 178/179f | 626 | 675 | 41 | — |

[1]NS = not sufficient similarity to score. Determined using the Martinez/Needleman-Wunsch algorithm with the default settings of minimum match 9, gap penalty 1.10, and gap length penalty 0.33.
[2]Determined using Lipman/Pearson alignments with the default settings of ktuple 2, gap penalty 4, and gap length 12.
[3]Four sizable gaps must be introduced into the B-FIV*12 to achieve optimal alignment. Aside from these gaps, the Y-FVw*12 and B-FIV*12 sequences have an S.I. of 58.
[4]Because of the short exon length, these values were not significant at the default setting. Significant similarities were found between the Ex7/cy2 sequences (S.I. = 67) when the minimum match was reduced to 6, indicating that relatedness of the genes extends through this short gene region.

Because the 3'-ends of the B and Rfp-Y loci were found to differ most extensively by both empirical and sequence comparisons, the two system-specific probes, 163/164f for Rfp-Y class I genes and 178/179f for B class I genes, were made corresponding to the respective 3' regions of the Rfp-Y and B-E loci. These two probes have a similarity index of 41 (see Table 1) and show distinct regions of unique sequence in a Martinez/Needleman-Wunsch DNA alignment.

FIG. 3 depicts the deduced amino acid sequences of Y-FVw*7 (SEQ ID NO: 3) and B-FIV*12 (SEQ ID NO: 4), aligned to illustrate regions of greatest sequence difference between the B and Rfp-Y class I loci. It is evident in FIG. 3 that the YFVw*7 and BFIV*12 genes share a great deal of identity in deduced amino acid sequence, however there are two regions where the amino acid sequences differ significantly. The α1 domain sequences diverge and are inherently polymorphic within both B and Rfp-Y loci. The latter half of the transmembrane domain and the three small cytoplasmic domains display significant divergence as do the intervening introns (see FIG. 2 and Table 1). The sequences of Y-FVw*7 and B-FIV*12 were obtained from the sequence of cosmid clone c17 and from Genbank M31012, respectively. Because the divergence is greatest in the 3' region of the genes (the latter half of the exon corresponding to the transmembrane domain and the exons of the cytoplasmic domains, intervening introns and 3'-untranslated regions) this region was chosen for the design of probes specific for the class I loci in each system.

Based on alignments revealing these areas of divergence, primer sets were designed to specifically amplify those regions in the Mhc B (primer 178(OLBF4TM); GGTGT-TGGATTCATCATCTAC; SEQ ID NO: 7 and primer 179 (RVBF43U); GCATAACAGTCAGCATAGGAA; SEQ ID NO: 8) and Rfp-Y (primer 163(OLYFVTM); CGCAGC-CCAACCTGATTCCCA; SEQ ID NO: 9 and primer 164 (RVYFV3U); TGTCAGCCCGAGGAGATGCAG; SEQ ID NO: 10) class I genes. Using the PCR, the 178/179 and 163/164 primer sets hybridize specifically to the genes in each gene cluster and amplify from the genomic DNA regions of the genes which are maximally different between the B region and the Rfp-Y region.

Thus, a probe was designed and cloned for each system which would be able to hybridize specifically to genes and gene fragments of each system without cross-hybridizing with the genes of the other system. The amplified and cloned regions encompass three exons corresponding to the cytoplasmic tail, surrounding introns and portions of the 3'-untranslated region. Clones from these regions form the probes for each system, termed the 178/179f (B system) probe (SEQ ID NO: 2) and the 163/164f (Rfp-Y system) probe (SEQ ID NO: 1). See FIGS. 4 and 5. The substrate DNA for production of the 163/164f probe was genomic DNA from a bird homozygous for the Y-F*w3 haplotype. While primer set 163/164 was used to produce the 163/164f probe, the 163/164f probe is shorter than the full expected sequence. For reasons that are not known, the fragment cloned from the 163/164 primer set PCR amplification was truncated at the 5' end. It is 120 nucleotides shorter than expected based on the primer 163 priming site. To have essentially the mirror image probe, the 178 priming site in the B-FIV sequence was located at a position nearly equivalent to the 5' start of 163/164f clone.

When tested in Southern hybridizations using DNA from fully pedigreed families for which the Mhc B and Rfp-Y types had been previously determined, the 178/179f probe was found to be specific for B class I genes and the 163/164f probe was found to be specific for Rfp-Y class I genes, confirming the specificity of each probe. Southern blot analysis to show the specificity of the probes was performed as follows. Samples containing 10 ug of genomic DNA were digested with a restriction enzyme. PstI, BglI, TaqI, PvuII, EcoRI and BamHI were used. The digest was subjected to electrophoresis in 0.8% agarose gels, and transferred to a non-charged hybridization membrane. The resolved fragments were stabilized in the membrane by UV-crosslinking and hybridized to each of the 178/179f and 163/164f probes. The probes (25–50 ng) were labeled by random priming with $\alpha^{32}$P-dCTP.

Hybridizations were carried out overnight in a rotating hybridization tube at 65° C. with 1–2×10$^6$ cpm/ml $^{32}$P-labeled probes in the presence of 5×SSPE (0.75 M NaCl, 0.05 M NaH$_2$PO$_4$, 5 mM EDTA), 5×Denhardt's solution (1 g/l Ficoll 400, 1 g/l polyvinylpyrrolidone, 1 g/l bovine serum albumin (Pentax Fraction V)), 100 pg/ml denatured salmon sperm DNA and 1% SDS. At this temperature and concentration of SSPE, hybridization is stringent so that the labeled probes will hybridize essentially only to identical or nearly identical sequences. Following the overnight hybridization, the membranes were washed at 65° C. at a lower salt concentration (75 mM NaCl, 7.5 mM sodium citrate with 1% SDS) to remove non-specifically adhering probe.

Figure 6:
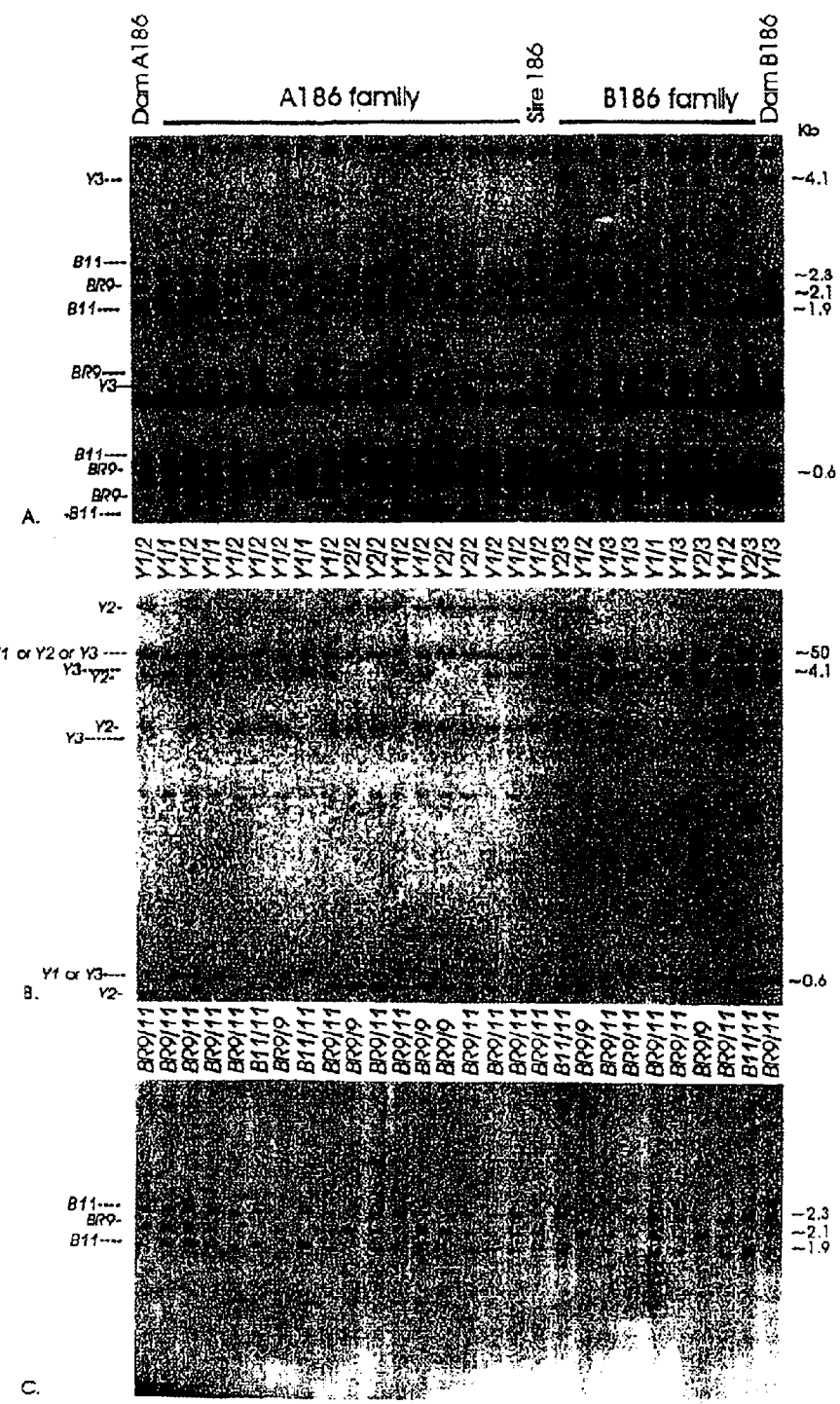
FIG. 6 shows three Southern hybridizations using the same filter containing BglI-digested DNA from two fully pedigreed families sharing the same sire hybridized successfully with (A) a prior art B system class II probe (B-LβII); (B) the Rfp-Y class I specific probe 163/164f and (C) the B system class I specific probe 178/179f.

Results demonstrated that each probe showed no cross reactivity to the other gene system. This is illustrated in FIG. 6, wherein PstI-digested DNA samples from the fully pedigreed A186 and B186 families were probed with 163/164f (FIG. 6B) and 178/179f (FIG. 6C). The patterns of the same DNA samples when hybridized with a prior art probe, full-length B class I probe (BF10) recognizing class Iα genes in both Rfp-Y and B is provided for comparison in FIG. 6A. The observed polymorphic restriction fragments reflect the genotypes in Rfp-Y and B respectively as previously determined. Miller et al., *Proc. Natl. Acad. Sci. USA* 91:4397–4401 (1994). There are no bands shared in common between the two patterns that represent Rfp-Y and B as revealed by the inventive probes.

The 163/164f probe for Rfp-Y genes was further tested for the ability to resolve polymorphic restriction fragment patterns in Southern hybridizations with additional Rfp-Y haplotypes to explore the potential range of utility of this probe. Genetic material from nine chickens, each possessing a different previously determined haplotype, was examined by Southern hybridization using the 163/164f probe. The probe was able to clearly resolve nine unique Rfp-Y class I TaqI restriction fragment patterns for the nine birds. (See FIG. 7.)

Interestingly, the number of TaqI and BglI restriction fragments is different among the haplotypes. For example, in FIG. 7 only two restriction fragments were revealed in haplotypes Yw*1 and Yw*7, but over ten fragments were found in haplotypes Yw*4 and Yw*6. Similar differences were found in the number of BglI restriction fragments (FIG. 8A). Similar procedures using the 178/179f probe for Mhc B class I genes confirmed this probe's ability to distinguish genetic variability in the B region (data not shown). Polymorphism in the B region, however, exists in other locations besides those recognized by the 178/179f probe (see, for example, FIG. 6A compared to FIG. 6C). Therefore, this probe reveals only a portion of the B class I genetic variability in an outbred population of birds. For example, one might find that several different B types defined by other methods would share the same restriction fragment pattern as revealed by the 178/179f probe with the most commonly used restriction enzymes.

Haplotyping may be performed with either of the probes of SEQ ID NO: 1 or SEQ ID NO: 2 individually or with both probes. Probe fragments and homologous probes also may be used as discussed above. Probes based on SEQ ID NOS: 1 and 2 but having non-hybridizing tails also are useful. Additional probes may also be used alongside the inventive probes if desired. Those of skill in the art will appreciate many variations of methods which are suitable. Chickens of any breed or type may be haplotyped or selected for breeding using the inventive probes. For example, the described methods may be applied to egg-laying stock, meat-type birds and dual purpose breeds, derivatives from these or any breed.

An advantage of these methods is that they can be applied to any chicken regardless of the breed, without knowledge of the exact nucleotide sequences in the polymorphic regions of the DNA being tested. The methods and probes can be used in the analysis of flocks for which no Mhc haplotype information exists and in many cases distinguish more different genotypes than existing prior art probes. In addition, the methods are easy to use and require only standard equipment for molecular biology. The methods can also be used initially to define the B and Rfp-Y genetics of a bird population to assist in the preparation of alloantisera for haplotyping.

Chickens are haplotyped using the inventive method according to the following general scheme. DNA is purified from a tissue sample from each individual bird to be tested. Genomic DNA samples for testing may be purified according to any convenient method which is known in the art and may be purified from any suitable tissue. Blood samples are conveniently used, however any tissue, such as wattle or comb tissue is suitable as well.

The DNA is cut into restriction fragments with one or more restriction endonuclease. BglI, PvuII, PstI, BamHI, EcoRI and TaqI are often used, however any restriction endonuclease or combination of restriction endonucleases which is suitable may be used. Haplotyping may be performed sequentially or in parallel with different endonucleases or combinations of endonucleases. Generally, enzymes that are intermediate in the frequency of cutting are suitable alternatives. Those of skill in the art are well aware of the variety of restriction enzymes available and their properties and thus are able to select any suitable enzyme. The restriction fragments are then resolved. Agarose gel (0.8–1.0%) electrophoresis is conveniently used. The electrophoresis may be accomplished on a slab gel, a tube gel or capillary electrophoresis may be performed. Generally, any method of separation is compatible with the use of these probes so long as the technique used is sufficient to resolve the restriction fragments and allows for hybridization of the probes.

The resolved fragments then most typically are transferred to and immobilized on a hybridization membrane. If it is desired to haplotype a sample with more than one probe, the restriction fragments may be transferred from the gel to multiple hybridization membranes, or alternatively, the DNA sample may be resolved in two lanes of the same or separate gels and then transferred to hybridization membrane(s). Filters may also be hybridized with one probe, the probe stripped, and a second hybridization carried out with an additional probe. A variety of techniques are well known by those of skill in the art and are contemplated for use with this invention.

After transfer, the restriction fragments may be stabilized in the hybridization filter if desired using any suitable technique. Exposure to UV light may be used, however any convenient method is contemplated for use with these methods. Alternative approaches also can be applied to reveal the resolved restriction fragments. For example, hybridizing the resolved DNA fragments with labeled probe may be done in the agarose gel, without transfer to a membrane. For this technique, fragments of the described probes are preferred, including synthetic oligonucleotides probes as small as 17 nucleotides.

The hybridization membranes containing the immobilized DNA fragments are then incubated with a labeled probe, according to known methods. A $^{32}$P label is most conveniently used, however other labels, both radioactive and non-radioactive, are available. Probes may be labeled with non-radioactive fluorescent tags (for example with ECF random prime labeling using products such as those available from Amersham Pharmacia Biotech) and detected in an imaging device such as Storm® fluorescence scanning system (Molecular Dynamics). Alternatively, probes can be labeled with chemiluminescent tags and visualized on film (for example, digoxigenin (DIG)-II-dUTP can be used and detected with an anti-DIG-alkaline phosphatase conjugate (Fab fragments) in highly specific immunoassays and visualized on film using the chemiluminescence substrates CSPD® or CDP-Star™ (Roche Molecular Biochemicals).

Incubation is performed under conditions which promote hybridization. Skilled artisans are well acquainted with such techniques and routinely adjust the incubation conditions for hybridization of probes so that optimal binding is achieved. Generally, stringent conditions provide good results. For $^{32}$P-labeled probes, these hybridizations are generally carried out in buffer containing 5×SSPE and 5×Denhardt's solution with 1% SDS and 100 µg/ml denatured salmon sperm DNA at 65° C. for 16 hours. The excess probe is removed by suitable washes (such as, for $^{32}$P-labeled probes, 0.5×SSC containing 1% SDS for one hour at 65° C., followed by a brief (1–2 minute) room temperature wash in 0.5×SSC to remove excess SDS), and an image of the bound labeled probe is created. Images from $^{32}$P-labeling may be collected on film or in a phosphor imaging device such as PhosphorImager™ (Molecular Dynamics/Amersham Pharmacia).

Alternatively, suitably specific conditions could be provided by hybridizing at 42° C. in the presence of 50% formamide (a compound that minimizes mismatched hybridization). Skilled works are familiar with adjusting conditions for hybridization and washing to achieve optimal results and such is considered routine.

Probes of the invention include the probe of SEQ ID NO: 1, SEQ ID NO: 2, probes with substantial homology (at least about 70%, or preferably at least about 90%) to SEQ ID NOS: 1 and 2 or fragments of such sequences. Probes having a longer sequence but including the above sequences may also be used, including sequences comprising adjacent regions of the gene of origin or its alleles. Generally, useful probes are limited by the similarity that exists between the class I genes in the B and Rfp-Y systems. Therefore, for example, it would be difficult to extend the length of the probes to include the entire transmembrane domain encoding exon and most of the more 5'-sequences since these regions generally show a high overall similarity index between the genes in the B and Rfp-Y systems. See Table 1.

Use of longer probes that encompass regions which are highly similar in the B and Rfp-Y genes would reveal mixtures of polymorphic and non-polymorphic fragments presenting allelic variabilities in both systems (as illustrated in FIG. 6A), making it more difficult to assign genotypes in either system with certainty. Extending the length of the probes to include more 3'-regions of the genomes is expected to be acceptable provided that the sequences in the more 3'-regions are sufficiently different between B and Rfp-Y loci and that the region contains polymorphic sequences within each system. Probes having non-hybridizing tails may be used, if desired, with the inventive methods. Fragments of the sequences SEQ ID NOS: 1 and 2 represented by oligonucleotides of as few as about 17 nucleotides to DNA fragments up to one nucleotide fewer than the entire sequence are contemplated for use with the invention and such fragments may be modified with non-hybridizing tails. Preferred probes are about 17 to about 1,000 base pairs, but most preferred probes are about 100 base pairs to about 1,000 base pairs in length and include at least 17 consecutive base pairs of the sequence of SEQ ID NOS: 1 or 2.

Probes which are substantially homologous to the sequences of SEQ ID NOS: 1 and 2 also are useful in haplotyping chickens according to the invention. Probes (and probe fragments) having insertions, deletions or substitutions may be useful so long as the probe used in able to hybridize with the genomic DNA restriction fragments of the appropriate system. Generally, useful probes have greater than about 70% homology and preferred probes have greater than about 90% homology to SEQ ID NO: 1 or SEQ ID NO: 2 or fragments thereof. Naturally, as skilled artisans are aware, hybridization conditions may be adapted to compensate for differences in the sequence of the probes and the existence of different degrees of possible mismatches.

The genotype of the individual chicken is determined from the restriction pattern revealed by the labeled probe. What constitutes a pattern corresponding to a particular class I gene haplotype is ascertained in different ways depending on what is known about the genetics of the population being tested. If fully pedigreed families are tested, the transfer of restriction fragment patterns from sire and dam to progeny can be followed. Which individual restriction fragment patterns are inherited together in a single pattern representing the linked genes of each allele in a haplotype, can be deduced or assigned with a high degree of certainty if inheritance is followed over three generations.

The pattern of two alleles in the diploid individual constitutes the individual's genotype. Within a family, there is a maximum of four alleles or haplotypes to follow. These patterns can be followed and assigned without much effort by those of skill in the art. In subsequent samples from birds with the same genetic make-up, the restriction patterns associated with the different haplotypes present in each DNA sample then are easily recognized by the skilled worker. It is possible to discover pedigree errors in some samples. For example, there may be samples among progeny which have restriction fragments not present in either the sire or dam. These are most likely due to pedigree errors, mislabeled samples or, rarely, chance recombination.

In some instances, it is not possible to examine all of the alleles of interest in fully pedigreed families to assign the restriction fragment pattern passed from one generation to the next. Most commercial chickens are produced by the crossing of closed lines of limited genetic variability. In this case, exact correspondence is not known between sires and dams and their progeny. There are, however, a finite member of haplotypes segregating within a line, and the number tends to be fewer, particularly when the lines are somewhat inbred. In such a case, the patterns associated with each haplotype can be deduced as a matter of routine from the patterns presented by the population.

Because one has no means of ascertaining how many alleles may be present in a larger or outbred population, assigning haplotypes to various restriction patterns within such a population is more time consuming. Therefore, it is preferable to select individuals from the population for pedigree mating and analysis. When this is not possible, the DNA samples may be analyzed several times using different restriction enzymes to develop confidence that all alleles have been revealed. Once the individual restriction fragments are sorted into patterns that are inherited as a group, the pattern assignment can be tested in the next generations. If necessary, a breeder or other worker could do limited pedigreed hatching to verify the inheritance patterns deduced from population studies.

Figure 7:
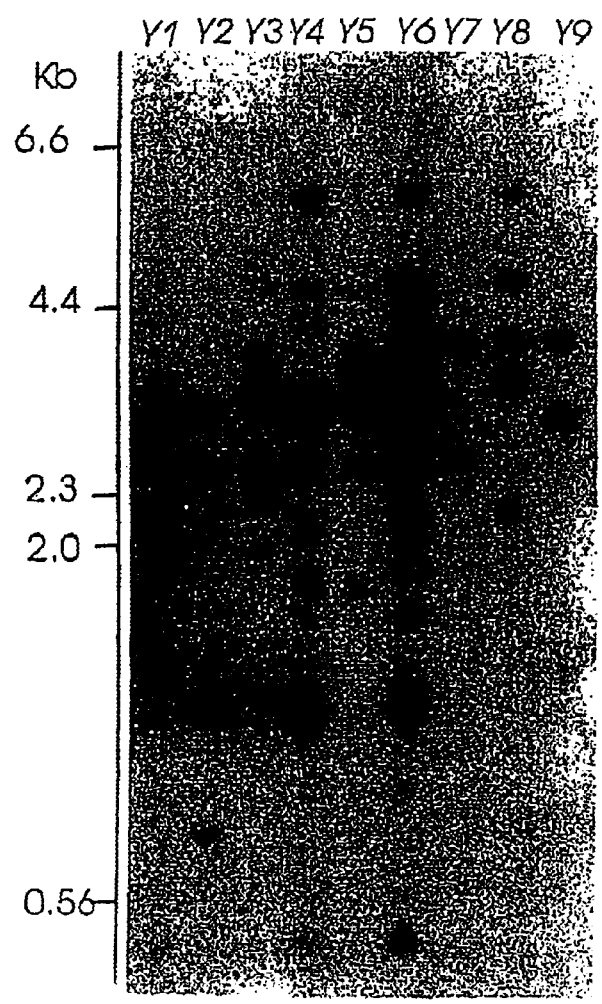
FIG. 7 is a Southern hybridization showing sequence variability in the Rfp-Y class I genes in nine different Rfp-Y haplotypes revealed by the 163/164f probe.
Figure 8:
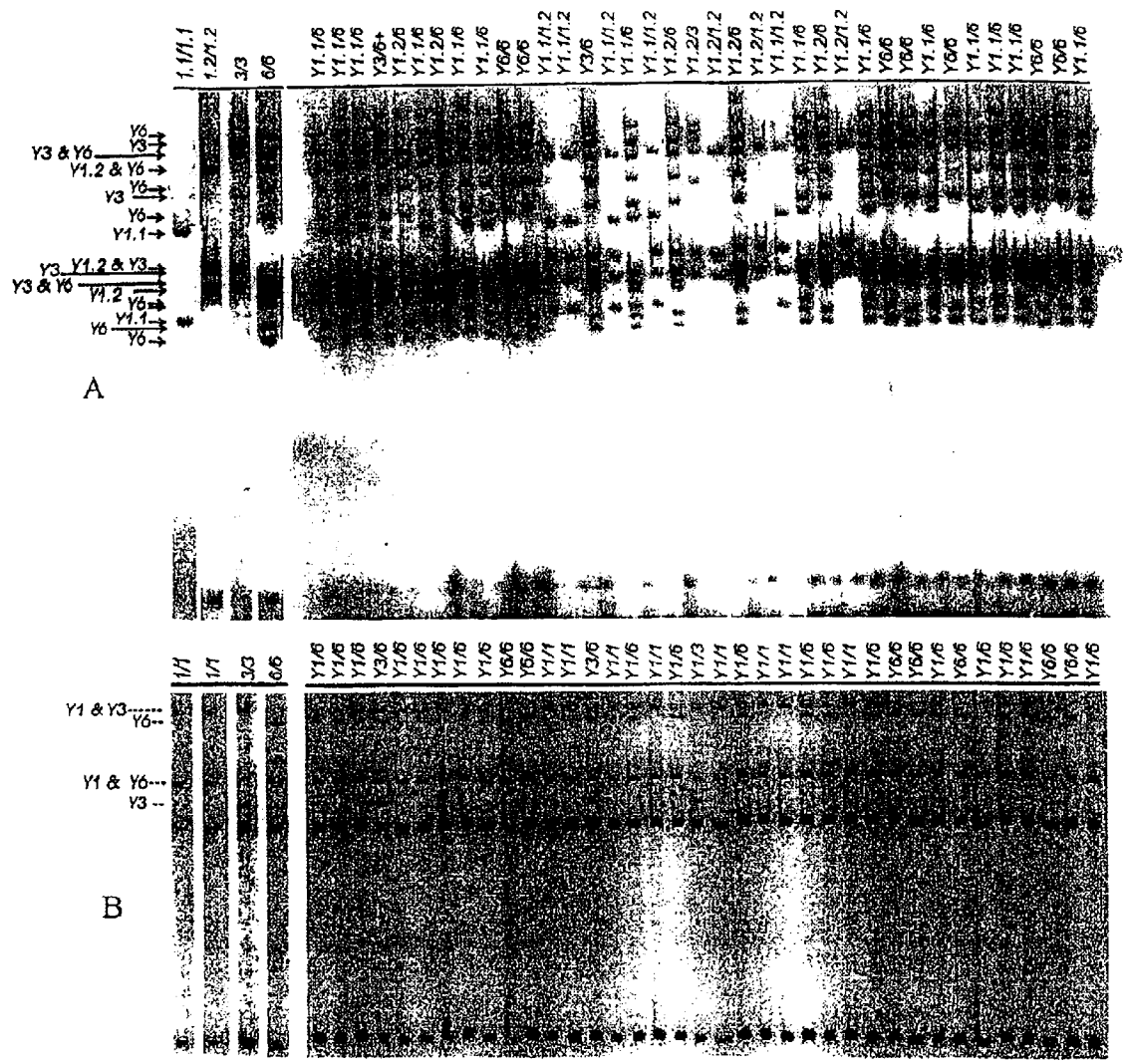
FIG. 8 shows two Southern hybridizations of the same filter containing Bgl-I digested DNA from genetically related birds hybridized (A) with the 163/164f probe and (B) with prior art probe B-LβII.

It was necessary to redefine a Y haplotype termed $Y^1$ based on an earlier restriction fragment with one probe into two different haplotypes $Y^{1.1}$ and $Y^{1.2}$ when two different patterns were found among the $Y^1$ samples using the 163/164f probe of the invention. An example of this is provided in FIG. 7. Compare FIG. 7A, in which the restriction fragments were probed with the 163/164f probe of the invention, to FIG. 7B, in which a prior art crosshybridizing B system probe was used. The 163/164f probe revealed additional genotypic differences and allowed four Rfp-Y haplotypes to be distinguished. In FIG. 7A, the 163/164f probe detected at least one unique restriction fragment for each haplotype, allowing them to be distinguished. Note that band sharing is more frequent with the prior art B-LβII probe (FIG. 7B) and $Y^{1.1}$ and $Y^{1.2}$ were not separated.

Because there are no standardized types in the Rfp-Y region, haplotyping in this region should be performed separately for each population. Therefore, each population of chickens will probably need to be analyzed using the strategies outlined above until more information about the different Y region haplotypes is obtained from different groups of chickens and more patterns have been assigned to haplotypes. The genotyping methods described herein may be used in connection with any species of domesticated fowl that possesses an Rfp-Y or B system. The methods herein disclosed are preferably used in genotyping programs for chickens, ring-necked pheasants or turkeys or any bird having an Rfp-Y system.

The 163/164 Y-specific probe can distinguish more polymorphic restriction fragments than prior art methods. Additionally, the 163/164f probe has the advantage of being specific for the Y system, avoiding the possibility of confusing crosshybridization with B system genes. The differences in Y haplotype distinguished with the 163/164f probe can predict differences in disease-resistance and mortality in a well recognized chicken disease model. This information, in addition to the demonstrated link between Rfp-Y haplotype and survivability of birds exposed to the commercially important Marek's disease and to other diseases of poultry, including avian Rous sarcoma virus, clearly demonstrates the usefulness of the 163/164f haplotyping probe in selection of breeding stocks for resistance to a variety of poultry diseases.

To utilize Rfp-Y haplotyping in a commercial breeding program, a database correlating Rfp-Y or B haplotypes to the desired disease resistance is created using studies correlating a bird's resistance to a disease with the haplotype revealed by the inventive probes. Breeders can then use this database in conjunction with information about Mhc haplotype in the available breeding lines to select parents for breeding. A database is created by challenging birds of known Mhc genotype with the disease of interest and correlating incidence, susceptibility or severity of disease with the Mhc genotype. The term "disease-resistance" or "disease-resistant" refers to birds which have a lower susceptibility to infection by the disease in question upon challenge, or which have a lower severity of the disease.

The following non-limiting examples are illustrative of the present invention. It is contemplated that modifications will readily occur to those skilled in the art within the spirit of the invention and the scope of the appended claims.

EXAMPLES

Example 1

Detection of Genetic Polymorphism in the Rfp-Y Region of Chickens of Known Haplotype Genomic DNA from several chickens of known Rfp-Y and B genotype was purified according to methods known in the art. To isolate the genomic DNA, small blood samples (about 100 μl packed cells) were digested in Proteinase K/SDS overnight at 55° C., extracted three times with phenol/dichloromethane then extracted twice more with dichloromethane and dialyzed extensively against 10 mM Tris HCl, pH 8, with 1 mM EDTA (TE). These DNA samples previously had been tested with a prior art B (B-LβII) system probe which crossreacts with Y system genes. A 10 μg sample of purified chicken DNA was digested with a restriction endonuclease (TaqI) using the buffer and conditions suggested by the manufacturer. The digested DNA was then concentrated by ethanol precipitation and resuspended in TE. The DNA digest was applied to a 0.8% agarose gel (20×21 cm) and separated at 60V in 89 mM Tris-HCl, 89 mM boric acid, pH 8.0, containing 2.5 mM EDTA (TBE). The gel was then stained with ethidium bromide and photographed under UV light. The gel was then treated for 10 minutes in 0.25 N HCl and the DNA transferred in 0.4 N NaOH to a hybridization membrane (Gene Screen™; NEN Life Science Products, Boston). After washing with distilled water and citrate buffer (0.3 M NaCl, 0.03 M sodium citrate, pH 7.0), the DNA was crosslinked to the membrane by short (2 minute) exposure to UV light in a UV-light DNA crosslinker (Stratalinker™; Stratagene, La Jolla, Calif.).

Labeled ($^{32}$P) 163/164f probe (SEQ ID No: 1) was hybridized to the DNA on the membrane filters under stringent conditions (65° C. overnight in 5×SSPE, 5×Denhardt's solution, 1% SDS with 100 μg/ml denatured salmon sperm DNA. The $^{32}$P-labeled probe was present at 1–2×10$^6$ cpm/ml. The hybridization was performed in Robbins™ hybridization tubes, containing 3 or 10 ml of the above hybridization solution in a hybridization incubator (Robbins Model 310, Sunnyvale, Calif.). The membranes then were treated with a stringent temperature wash at 65° C. in 75 mM NaCl, 7.5 mM sodium citrate, pH 7. Images of the hybridized membranes were then developed, revealing different multiple bands of genomic chicken DNA for each individual chicken tested. The genetic fingerprint of each individual chicken shown identifies the haplotype of that individual in the Rfp-Y region. See FIG. 7.

Example 2

Determination of the B Region Genotype of the Progeny of Chickens of Known Haplotype The method of Example 1 was repeated on two serologically typed families having the same sire but two different dams, substituting the 178/179f probe for the 163/164f probe. See FIG. 6C. In this example, however, PstI was the restriction enzyme, and the buffer and conditions suggested by the manufacturer were used for digestion. The samples analyzed here were assigned to B haplotypes based on the names from existing serological reagents. In FIG. 6C, there is a clear correspondence between the BR9 haplotype and one restriction fragment and the B11 haplotype and a doublet of restriction fragments, one larger and one smaller than the band corresponding to BR9. It is therefore possible to easily determine which B types were inherited by each of the progeny. The genotype is indicated along the top of FIG. 6C.

Example 3

Determination of the Rfp-Y Haplotype of Individual Chickens

The methods of Example 1 were repeated using BglI-digested DNA samples from a cohort of chickens derived from a previously typed parental generation, for which there is some pedigree data. The exact sire and dam for each individual was not known, however. See FIG. 8. The leftmost four lanes indicate the deduced patterns for the indicated homozygotic conditions. These four patterns are seen to be combined variously in patterns interpreted as those of heterozygous individuals. The Y genotypes deduced from the multiple patterns present are listed across the top right portion of FIG. 8A. Because there are only four patterns segregating in this population, the various heterozygote combinations were easily determined. The rare pattern, $Y^3/Y^{6+}$, was detected in this population (see fourth lane). Only three Rfp-Y haplotypes could be deduced when restriction fragment patterns in the same samples were probed with a prior art B-Lβ11 probe that hybridizes to both B and Rfp-Y restriction fragments. Compare FIG. 8A to FIG. 8B.

What is claimed is:

1. A probe which consists essentially of 17 to about 1,000 consecutive nucleotides of the chicken class I genes in the B or Rfp-Y system wherein at least 17 consecutive nucleotides of said probe are 17 consecutive nucleotides of SEQ ID NO: 2.

2. A probe according to claim 1, which comprises about 100 to about 1,000 nucleotides.

3. The probe of SEQ ID NO: 1.

4. The probe of SEQ ID NO: 2.

5. A fragment of the probe according to claim 4, which comprises 17 to about 674 nucleotides.

6. A method for determining the Mhc genotype of a chicken, comprising:
   (a) providing a genomic DNA sample from at least one chicken;
   (b) digesting said genomic DNA sample with at least one restriction endonuclease to obtain restriction fragments;
   (c) resolving said restriction fragments;

(d) optionally transferring said resolved restriction fragments to one or more hybridization membranes and optionally immobilizing said transferred restriction fragments on said hybridization membranes;

(e) incubating said resolved restriction fragments with a first probe according to claim 3 under conditions such that said first probe hybridizes with said resolved restriction fragments, wherein said first probe is labeled;

(f) washing said resolved restriction fragments to remove unhybridized first probe;

(g) creating an image of said labeled first probe hybridized to said resolved restriction fragments such that a restriction pattern is formed;

(h) determining the Mhc genotype of said at least one chicken from said restriction pattern; and (i) optionally stripping said first probe and incubating said resolved restriction fragments with a second probe according to claim 3 under conditions such that said second probe hybridizes with said resolved restriction fragments, wherein said second probe is labeled and repeating steps (f)–(h).

7. A method according to claim 6, wherein said resolved restriction fragments are incubated with one probe.

8. A method according to claim 6, wherein said resolved restriction fragments are incubated with a first probe and a second probe.

9. A method according to claim 8, wherein one of said first probe and said second probe is specific for the Rfp-Y system and the other of said first probe and said second probe is specific for the B system.

10. A method according to claim 8, wherein one of said first probe and said second probe is SEQ ID NO: 1 and the other said first probe and said second probe is SEQ ID NO: 2.

11. A method for selecting a chicken which is resistant to a preselected disease, comprising:

(a) determining the Mhc genotype of at least one chicken according to the method of claim 6; and (b) correlating said Mhc genotype to said resistance to said preselected disease.

12. A probe which consists essentially of 17 to about 1,000 consecutive nucleotides of the chicken Rfp-Y or B class I genes wherein at least 17 consecutive nucleotides of said probe are 17 consecutive nucleotides of SEQ ID NO: 1, and a non-hybridizing tail.

* * * * *

UNITED STATES PATENT AND TRADEMARK OFFICE
CERTIFICATE OF CORRECTION

PATENT NO. : 6,716,972 B2
DATED : April 6, 2004
INVENTOR(S) : Miller et al.

It is certified that error appears in the above-identified patent and that said Letters Patent is hereby corrected as shown below:

Column 29,
Lines 6 and 20, "claim 3" should read -- claim 1 --;

Column 30,
Line 10, insert -- of -- after "other".

Signed and Sealed this

Thirtieth Day of November, 2004

JON W. DUDAS
*Director of the United States Patent and Trademark Office*

SEQUENCE LISTING

<160> NUMBER OF SEQ ID NOS: 11

<210> SEQ ID NO 1
<211> LENGTH: 626
<212> TYPE: DNA
<213> ORGANISM: Gallus sp.

<400> SEQUENCE: 1

```
ggggagaaag cgggagctgc aggtggggcc tggacccct tgggaatgcc catgttctga     60
catgagctta atgttcacac ttctttctat ctgtagggaa ggagaagaag ggttatgaag   120
cagcgccagg tgagtgccaa gggcagcgct ttaccctgcc agtgcttggg gtcagggcac   180
tctggggccc ctcgttgctt ttggggtcac agtgcaggtg gtggcatgat gctccatgcc   240
ccacagcgag cacagagcca gggctcatgg ctctccctcc cttgcaggcc agggcggaga   300
atccagcata tcggccacag gtatagtgtg gaatgggggt tcaggagggg tccctgtggt   360
tggagcattc ccagttccct gcactcccct gttggaccca cggccgggc aatactgggc   420
ccaaccctcc ctggagaacc cccagggtgg tgagtcggga cggggacgtg gtcccatatg   480
acaccacctc ttctcacccg cacaggaagt gaacttccct tctgagtgct gtgttacttc   540
agccagccct gcatgcatgt gtttggagtg tgtgggtgtg tgtatctcag tgtgtgctca   600
acttcctgca tctcctcggg ctgaca                                        626
```

<210> SEQ ID NO 2
<211> LENGTH: 675
<212> TYPE: DNA
<213> ORGANISM: Gallus sp.

<400> SEQUENCE: 2

```
ggtgttggat tcatcatcta cagacgccac gcaggtaaaa gcagaggggt gcaggcgggc     60
agtggtggca gtgggggat ctgggtcccc cttgggagcc ctcagcctgg ctgtgatgtg   120
aacctgtgtt gattcatctc tctgtctgca gggaagaagg ggaagggcta caacatcgcg   180
cccggtgagt gatgagggca gcgctgtccc ccacctctgc ccagtgccag ggcggtcctg   240
gggtctgcac tttctcccag ggtacccatt cctggtgctt ggggctgctc cacgccccat   300
agggagcaca gggctgggtc tcacagctgt tcctcccta tagacaggga aggtggatcc   360
agcagctcga gcacaggtgc ggtgtggggc tgtgggttgg gagggtccg tgtgctctct   420
gtggtactgc ccagggctgg gctatgctgg ggctctgcgg ggagaccccc ggagcagagg   480
gttgggatgt gaacatgggc cccgtgggac accatctctt ctcatcccca cagggagcaa   540
cccctccatc tgagtgctgt gcttcagcat gcacgaagcc aacagtccac accagcattt   600
ggggtcagtg atgggcacag ccccatcctc ttgacctctc acatctcgtt ctgcttccta   660
tgctgactgt tatgc                                                     675
```

<210> SEQ ID NO 3
<211> LENGTH: 332

<212> TYPE: PRT
<213> ORGANISM: Gallus sp.

<400> SEQUENCE: 3

```
Gly Ser His Ser Leu Arg Tyr Phe Leu Thr Gly Met Thr Asp Pro Gly
1               5                   10                  15

Pro Gly Met Pro Arg Phe Val Ile Val Gly Tyr Val Asp Asp Lys Ile
            20                  25                  30

Phe Gly Thr Tyr Asn Ser Lys Ser Arg Thr Ala Gln Pro Ile Val Glu
        35                  40                  45

Met Leu Pro Gln Glu Asp Gln Glu His Trp Asp Thr Gln Thr Gln Lys
    50                  55                  60

Ala Gln Gly Gly Glu Arg Asp Phe Asp Trp Asn Leu Asn Arg Leu Pro
65                  70                  75                  80

Glu Arg Tyr Asn Lys Ser Lys Gly Ser His Thr Met Gln Met Met Phe
                85                  90                  95

Gly Cys Asp Ile Leu Glu Asp Gly Ser Ile Arg Gly Tyr Asp Gln Tyr
            100                 105                 110

Ala Phe Asp Gly Arg Asp Phe Leu Ala Phe Asp Met Asp Thr Met Thr
        115                 120                 125

Phe Thr Ala Ala Asp Pro Val Ala Glu Ile Thr Lys Arg Arg Trp Glu
130                 135                 140

Thr Gly Thr Tyr Ala Glu Arg Trp Lys His Glu Leu Gly Thr Val
145                 150                 155                 160

Cys Val Gln Asn Leu Arg Arg Tyr Leu Glu His Gly Lys Ala Ala Leu
                165                 170                 175

Lys Arg Arg Val Gln Pro Glu Val Arg Val Trp Gly Lys Glu Ala Asp
            180                 185                 190

Gly Ile Leu Thr Leu Ser Cys His Ala His Gly Phe Tyr Pro Arg Pro
        195                 200                 205

Ile Thr Ile Ser Trp Met Lys Asp Gly Met Val Arg Asp Gln Glu Thr
    210                 215                 220

Arg Trp Gly Gly Ile Val Pro Asn Ser Asp Gly Thr Tyr His Ala Ser
225                 230                 235                 240

Ala Ala Ile Asp Val Leu Pro Glu Asp Gly Asp Lys Tyr Trp Cys Arg
                245                 250                 255

Val Glu His Ala Ser Leu Pro Gln Pro Gly Leu Phe Ser Trp Glu Pro
            260                 265                 270

Gln Pro Asn Leu Ile Pro Ile Val Ala Gly Ala Val Val Ala Ile Val
        275                 280                 285

Ala Val Ile Ala Ala Val Val Gly Leu Val Val Trp Lys Ser Lys Ser
    290                 295                 300

Gly Lys Glu Lys Lys Gly Tyr Glu Ala Ala Gly His Asp Gly Glu
305                 310                 315                 320

Ser Ser Gly Ser Ala Thr Gly Ser Glu Pro Ser Ile
                325                 330
```

<210> SEQ ID NO 4
<211> LENGTH: 334
<212> TYPE: PRT
<213> ORGANISM: Gallus sp.

<400> SEQUENCE: 4

```
Glu Leu His Thr Leu Arg Tyr Ile Gln Thr Ala Met Thr Asp Pro Gly
1               5                   10                  15
```

-continued

```
Pro Gly Gln Pro Trp Phe Val Thr Val Gly Tyr Val Asp Gly Glu Leu
             20                  25                  30

Phe Val His Tyr Asn Ser Thr Ala Arg Arg Tyr Val Pro Arg Thr Glu
             35                  40                  45

Trp Ile Ala Ala Lys Ala Gln Glu Gln Tyr Asp Thr Gly Thr Gln Lys
 50                  55                  60

Ile Gly Gly Gly Asn Arg Gln Ile Asp Arg Glu Leu Asn Gly Ile Pro
 65                  70                  75                  80

Gln Arg Tyr Asn Lys Gln Thr Gly Gly Ser His Thr Val Gln Trp Met
                 85                  90                  95

Tyr Gly Cys Asp Ile Leu Glu Gly Gly Pro Ile Arg Gly Tyr Tyr Gln
            100                 105                 110

Met Ala Tyr Asp Gly Arg Asp Phe Thr Ala Phe Asp Lys Gly Thr Met
            115                 120                 125

Thr Phe Thr Ala Ala Val Pro Glu Ala Val Pro Thr Lys Arg Lys Trp
            130                 135                 140

Glu Glu Glu Ser Glu Pro Glu Arg Trp Lys Asn Tyr Leu Glu Glu Thr
145                 150                 155                 160

Cys Val Glu Trp Leu Arg Arg Tyr Val Glu Tyr Gly Lys Ala Glu Leu
                165                 170                 175

Gly Arg Arg Glu Arg Pro Glu Val Arg Val Trp Gly Lys Glu Ala Asp
            180                 185                 190

Gly Ile Leu Thr Leu Ser Cys Arg Ala His Gly Phe Tyr Pro Arg Pro
            195                 200                 205

Ile Val Val Ser Trp Leu Lys Asp Gly Ala Val Arg Gly Gln Asp Ala
            210                 215                 220

His Ser Gly Gly Ile Val Pro Asn Gly Asp Gly Thr Tyr His Thr Trp
225                 230                 235                 240

Val Thr Ile Asp Ala Gln Pro Gly Asp Gly Asp Lys Tyr Gln Cys Arg
                245                 250                 255

Val Glu His Ala Ser Leu Pro Gln Pro Gly Leu Tyr Ser Trp Glu Pro
            260                 265                 270

Pro Gln Pro Asn Leu Val Pro Ile Val Ala Gly Val Ala Val Ala Ile
            275                 280                 285

Val Ala Ile Ala Ile Met Val Gly Val Gly Phe Ile Ile Tyr Arg Arg
            290                 295                 300

His Ala Gly Lys Lys Gly Lys Gly Tyr Asn Ile Ala Pro Asp Arg Glu
305                 310                 315                 320

Gly Gly Ser Ser Ser Ser Thr Gly Ser Asn Pro Ala Ile
                325                 330
```

<210> SEQ ID NO 5
<211> LENGTH: 2470
<212> TYPE: DNA
<213> ORGANISM: Gallus sp.

<400> SEQUENCE: 5

```
gatctgcctg gcgcccggtg acgtcacccg cggtcacgga ctccattggc ggggagaggc      60
ggaggcacca atgggggcgc ggggcggtgc ctgggtagtc cacggagcgg cgccgagcgg     120
cgccatgggt ccgagcgagg tggtggtgct ggggctgctg ctgggcgccc tgggcgcggc     180
ggagtgcggt gagtgctgcg ggatcgggct gccccggca ccgggaccccg cggctcctcg     240 ctccccgacg ccggggctgc gtccgcggga ccccacccg cggctcacgg ctccgacgcc     300
gtctgtcccc gcagggtcgc actccctgcg ctacatcctg accgggatga cggatcccgg     360
```

```
ccccgggatg ccgcggttcg tgatcgtcgg gtacgtggac gacaaaatct tcggtaccta      420
caacagtaag agcaggactg cacagcctat cgtggagatg ctgccgcagg aggaccagga      480
gcactgggac acgcagaccc agaaggcgca gggcggtgag cggattttg  actggaacct      540 gaacaggctg ccggaacgct acaacaaaag taaaggtgag cgtgggggaa gctgcagcgc      600
gatgcgtctg ggacaggagc tctgtgtgcc gagggtgtcc gccagcccca ctgaggtgtg      660
gccgtgcccc acgccagct  gtgctgggcc gtccatgtgt ggtggcactg tccctgggcc      720
gccctgctcc tgcgcccacc caccccaccc cagcctcatg gcactcgcgg tgccccacag      780
ccctagaagc ctctcaccta ttactctggc tgtgcctcag gtctcacac  gatgcagatg      840 atgtttggct gtgacatcct ggaggacggc agcatccgag gtacgatca  gtatgcattt      900 gatgggaggg acttccttgc ctttgatatg gacacgatga cgttcaccgc ggcggatcca      960
gtggctgaaa tcaccaagag gagatgggag acagaaggga cgtatgctga gagatggaag     1020
catgagctgg ggactgtctg tgttcagaac ttgaggagat acctggagca tgggaaggca     1080
gcgctgaaaa ggagaggtga ggatggggag gggacgtggg gctgggctgg gtgtgggggca    1140 gaggctcagt gtggggtgct cagcccggcc caccacgtca cccacctgca gtgcagcccg     1200
aggtgcgagt gtggggaag  gaggccgatg ggatcctgac cttgtcctgc cacgctcacg     1260
gtttctaccc gcggcccatc accatcagct ggatgaagga cggcatggtc cgggaccagg     1320
agacccgctg ggggggcatc gtgcccaaca gcgatggcac ctaccacgcc tcggctgcca     1380
ttgatgtgct gccggaggat ggggacaagt attggtgccg cgtggagcac gccagcctgc     1440
cccagcctgg tctcttctca tggggtgagc tggcagcgtg gggcacgggg ggttgggatt     1500
cgcaggctgc cccttccttt actgacaacg gcgctctcct ccagagccgc agcccaacct     1560
gattcccatt gtggcagggg cggtcgttgc catcgtggct gtcatcgctg cggtcgttgg     1620
attggtggtg tggaagagca agtcaggtaa aggtagtgag ctgggggggag aaagcgggag    1680 ctgcaggtgg ggcctggacc cccttgggaa tgcccatgtt ctgacatgag cttaatgttc     1740 acacttctttt ctatctgtag ggaaggagaa gaagggttac gaagcagcag caggtgagtg    1800
ccaagggcag cgctgtcccc tgccagtgct tggggtcagg gcactctggg gccccctcgtt    1860 gctttgggt  aatagtgcta gtggtggcat gatgctccat gccccatagc gagcacagag     1920
ccagggctca tggctctccc tcccttgcag gccacgacgg agaatccagt ggctcggcca     1980
caggtacagt gtggaacggg ggctcaggag gggtccctgt ggttggagcg gtcccagttc     2040
cctgcactcc cccgttgggc ccacggccgg ggcaatactg ggcccagccc tcctgctga     2100 accccagggg tggtgagtca ggatgtggat gtggcccac  gtgacaccat ctcttctcac     2160
ccgcacagga agtgaacctt ccatctgagt gctgtgctgc agtagccagc cttgcatgca     2220
cgtgtttgga gtttgagggt gtgtgcatct ctgtttgctc aactcctgca tctcctcggg     2280
ctgacacagt gtgtgtcttc aagtcaaata aaccccagca ctgtggattg ctggtttgca     2340
gctcagcctg cgtggtgtct gatttgggt  gggggaatc  gcgtcccgtt cagcagctca     2400
gggcctggat ggggccccgt ggtgggtatc cactgctctg ctctcaccca tcaggctgcc     2460
gcgtgcattg                                                            2470
```

<210> SEQ ID NO 6
<211> LENGTH: 2482
<212> TYPE: DNA
<213> ORGANISM: Gallus sp.

<400> SEQUENCE: 6

```
attctgcctg gcgcccgatg acgtcacata aaactccaac taccattggc ggagaggcga        60
cggaggagcc aatggggcg cggggcgggg cggaggagta ggaaaagctg aaggagctgc       120
gctgggtgcg gcggacttga gagtgcagcg gtgcgaggcg atgggccgt gcggggcgct       180
gggcctgggc ctgctgctcg ccgccgtgtg cggggcggcg gcccccggtg agtgcggccg      240
gaccgggacc cctcccccgc ccgtaacccc accccggggc tgtgtccgtg ggatcctgag      300
acccacaccc gcggctcacg gcccgctgtg ctccgtcccc gcagagctcc ataccctgcg      360
gtacatccaa acggcgatga cggatcccgg ccccgggcag ccgtggttcg tgactgtggg      420
gtacgtggac ggggaactct tcgtgcacta acagcacc gcgcggaggt acgtgccccg       480
caccgagtgg atagcggcca aggcggacca gcagtactgg gatggacaga cgcagatcgg      540
acagggcaat gagcagattg accgcgagaa cctgggcata ctgcagcggc gctacaacca      600
gaccggcggt gagcacggcc ggggccgcgg ctccgtgggt gtgggatggg ctccatgcgc      660
agtgccgccc acaccccca ggcctggccc tgccggcgg caccgtcccg gggctgcccg       720
tcacagcccc accgcgctcg gggtgccgcg tcccgggggg accccaaccc atcccgctg      780
cagtgggagc cccggagccg gaggggcccc tcacccctg cccggctgtg tttcagggtc      840
tcacacggtg cagtggatgt acggctgtga catcctcgag ggcggcccca tccggggta       900
ttatcagatg gcctacgatg ggagagactt cactgccttc gacaaaggca cgatgacgtt      960
cactgcggca gttccagagg cagttcccac caagaggaaa tggaggaag agagtgaacc      1020
tgagaggtgg aagaattacc tggaggaaac ctgcgtggag tggctgcgga gatacgtgga     1080
atacgggaag gctgagctgg gcaggagagg tgagcggggt ggggggggga gcggctgcag     1140
tgtgggctg gacgtggggc gggggctcag cgtgggagc tcagcccggc cctcactgcc      1200
gcccgcccgc agagcggccc gaggtgcgag tgtggggaa ggaggccgac gggatcctga     1260
ccttgtcctg ccgcgctcac ggcttctacc cgcggcccat cgttgtcagc tggctgaagg     1320
acggcgcggt gcggggccag gacgcccact cggggggcat cgtgcccaac ggcgacggca     1380
cctaccacac ctgggtcacc atcgatgcgc agccggggga cggggacaag taccagtgcc     1440
gcgtggagca cgccagcctg ccccagcccg gcctctactc gtggggtgag tgaggggatg     1500
tggggctggg gggctgcggg ctgccccttc ccctgctgat ggccccgctc tcccccagag     1560
ccgccacagc caacctggt gcccatcgtg gcggggtgg ccgtcgccat gtgccatt        1620
gccatcatgg ttggtgttgg attcatcatc tacagacgcc atgcaggtaa aaacagaggg     1680
gtgcaggcgg gcagtggggg gatctgggtc ccccttggga gccctcagcc tggctgtgat     1740
gtgaacctgt gctgaagcat ctctctgtct gcagggaaga aggggaaggg ctacaacatc     1800
gcgcccggtc agtgatgagg gcagcgctgt ccccaccct tgcccagtgc cagggcggtt      1860
gcagggtctg cactttctcc caggtaccc attcctggtg cttgggctg ctccacgccc      1920
cataggagc acagggctgg atctcacagc tgttcctccc ttatagacag gaaggtgga     1980
tccagcagct cgagcacagg tgcgtgtggg gctgtgggtt gggagggtc cgtgtgctct     2040
ctgtggtact gccagggct gggctatgct ggggctctgc ggggagaccc ccggagcaga     2100
gggttgggat gtgaacctgg ccccgtggga catcatccct tctcatccca cagggagcaa     2160
ccccgccatc tgagtgctgt gcttcagcct gcaaggagcc aacagtccac accagcattt     2220
ggggtcagtg atgggcacag cccatcctc ttgacctctc acatctcatt ctgcttccta     2280
tgctgactgt tatgctttgc ctgcactgct tctaggcaaa taaatgatg ggccattctg       2340
```

-continued

```
tggctcagct tgcctgcagt ctgcactgtg ctgtggttgg ggatggggtg gatgagggga    2400
ccgtgtcagt ttggctgctc agggtgcaga tgtggccctg tgctgagtac ccactgccct    2460
cccctcttct atctgcccgc tg                                             2482

<210> SEQ ID NO 7
<211> LENGTH: 21
<212> TYPE: DNA
<213> ORGANISM: Artificial Sequence
<220> FEATURE:
<223> OTHER INFORMATION: amplification primer 178 (OLBF4TM)

<400> SEQUENCE: 7
ggtgttggat tcatcatcta c                                              21

<210> SEQ ID NO 8
<211> LENGTH: 21
<212> TYPE: DNA
<213> ORGANISM: Artificial Sequence
<220> FEATURE:
<223> OTHER INFORMATION: amplification primer 179 (RVBF43U)

<400> SEQUENCE: 8
gcataacagt cagcatagga a                                              21

<210> SEQ ID NO 9
<211> LENGTH: 21
<212> TYPE: DNA
<213> ORGANISM: Artificial Sequence
<220> FEATURE:
<223> OTHER INFORMATION: amplification primer 163 (OLYFVTM)

<400> SEQUENCE: 9
cgcagcccaa cctgattccc a                                              21

<210> SEQ ID NO 10
<211> LENGTH: 21
<212> TYPE: DNA
<213> ORGANISM: Artificial Sequence
<220> FEATURE:
<223> OTHER INFORMATION: amplification primer 164 (RVYFV3U)

<400> SEQUENCE: 10
tgtcagcccg aggagatgca g                                              21

<210> SEQ ID NO 11
<211> LENGTH: 6
<212> TYPE: DNA
<213> ORGANISM: Gallus sp.

<400> SEQUENCE: 11 gggctg                                                               6
```